United States Patent
Pible et al.

(10) Patent No.: US 11,177,017 B2
(45) Date of Patent: Nov. 16, 2021

(54) METHOD OF DECONVOLUTION OF MIXED MOLECULAR INFORMATION IN A COMPLEX SAMPLE TO IDENTIFY ORGANISM(S)

(71) Applicant: Commissariat a l'Energie Atomique et aux Energies Alternatives, Paris (FR)

(72) Inventors: Olivier Pible, Bedarrides (FR); Jean Armengaud, Villeneuve-lez-Avignon (FR); François Allain, Agneaux (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 595 days.

(21) Appl. No.: 14/910,425

(22) PCT Filed: Jul. 30, 2014

(86) PCT No.: PCT/IB2014/063560
§ 371 (c)(1),
(2) Date: Feb. 5, 2016

(87) PCT Pub. No.: WO2015/019245
PCT Pub. Date: Feb. 12, 2015

(65) Prior Publication Data
US 2016/0300011 A1    Oct. 13, 2016

(30) Foreign Application Priority Data

Aug. 6, 2013   (EP) ..................................... 13306125

(51) Int. Cl.
*G16B 10/00*   (2019.01)
*G16B 20/00*   (2019.01)

(52) U.S. Cl.
CPC ............. *G16B 10/00* (2019.02); *G16B 20/00* (2019.02)

(58) Field of Classification Search
CPC ......... G06F 19/14; G06F 19/18; G16B 10/00; G16B 20/00; G16B 99/00
See application file for complete search history.

(56) References Cited

U.S. PATENT DOCUMENTS

| | | | |
|---|---|---|---|
| 6,738,502 B1 * | 5/2004 | Coleman .............. | G01N 21/274 382/133 |
| 8,224,581 B1 | 7/2012 | Wick et al. | |
| 8,412,464 B1 * | 4/2013 | Wick ........................ | C12Q 1/04 435/6.14 |
| 2014/0249036 A1 * | 9/2014 | Fry ......................... | C12Q 1/689 506/2 |

OTHER PUBLICATIONS

Nesvizhskii A.I. (2007) Protein Identification by Tandem Mass Spectrometry and Sequence Database Searching. In: Matthiesen R. (eds) Mass Spectrometry Data Analysis in Proteomics. Methods in Molecular Biology, vol. 367. Humana Press. (Year: 2007).*

Voelkerding et al. Next-generation sequencing: From basic research to diagnostics. Clinical Chemistry, vol. 55, No. 4, pp. 641-658, 2009. (Year: 2009).*

Guarino et al. Peptidomic approach, based on liquid chromatography/electrospray ionization tandem mass spectrometry, for detecting sheep's milk in goat's and cow's cheeses. Rapid Communications in Mass Spectrometry, vol. 24, pp. 705-713, 2010. (Year: 2010).*

Baud et al. Proteomics-based refinement of Deinococcus deserti genome annotation reveals an unwonted use of non-canonical translation initiation codons. Molecular & Cellular Proteomics, vol. 9, pp. 415-426, 2010. (Year: 2010).*

Gallien et al. Selected reaction monitoring applied to proteomics. Journal of Mass Spectrometry, vol. 46, pp. 298-312, 2011. (Year: 2011).*

Armengaud, J. Microbiology and proteomics, getting the best of both worlds! Environmental Microbiology, vol. 15, No. 1, pp. 12-23, 2013, published online Jun. 9, 2012. (Year: 2012).*

Wasinger et al. Current status and advances in quantitative proteomic mass spectrometry. International Journal of Proteomics, Article ID 180605, printed as pp. 1-12, Mar. 6, 2013. (Year: 2013).*

Ewing et al. Base-calling of automated sequencer traces using Phred. II. Error Probabilities. Genome Research, vol. 8, pp. 186-194, 1998. (Year: 1998).*

Amann et al. Phylogenetic identification and in situ detection of individual microbial cells without cultivation. Microbiology Reviews, vol. 59, No. 1, pp. 143-169, 1995. (Year: 1995).*

Entry for "Graphical User Interface (GUI)" in Technopedia (www.technopedia.com), 2012, printed as p. 1/2-2/2 (Year: 2012).*

Dworzanski et al., "Mass Spectrometry-Based Proteomics Combined with Bioinformatic Tools for Bacterial Classification," Journal of Proteome Research, 5: 76-87 (2006).

Dworzanski et al., "Identification of Bacteria Using Tandem Mass Spectrometry Combined with a Proteome Database and Statistical Scoring," Analytical Chemistry, 76: 2355-2366 (2004).

Ribeca et al., "Computational challenges of sequence classification in microbiomic data," Briefings in Bioinformatics, 12: 614-625 (2011).

(Continued)

*Primary Examiner* — Jennifer Dunston
(74) *Attorney, Agent, or Firm* — Morgan, Lewis & Bockius LLP

(57) ABSTRACT

The present invention relates to methods to determine the identity of one or more organisms present in a sample (if these are already reported in a taxonomic database) or the identity of the closest related organism reported in a taxonomic database. The present invention does this by comparing a data set acquired by analyzing at least one component of the biological sample to a database, so as to match each component of the analyzed content of the sample to one or more taxon(s) and then collating the phylogenetic distance between each taxa and the taxon with the highest number of matches in the data set. A deconvolution function is then generated for the taxon with the highest number of matches, based on a correlation curve between the number of matches per taxon (Y axis) and the phylogenetic distance (X axis), the outcome of this function providing the identity of the organism or the closest known organism to it.

11 Claims, 15 Drawing Sheets

(56) References Cited

OTHER PUBLICATIONS

Figure 1:
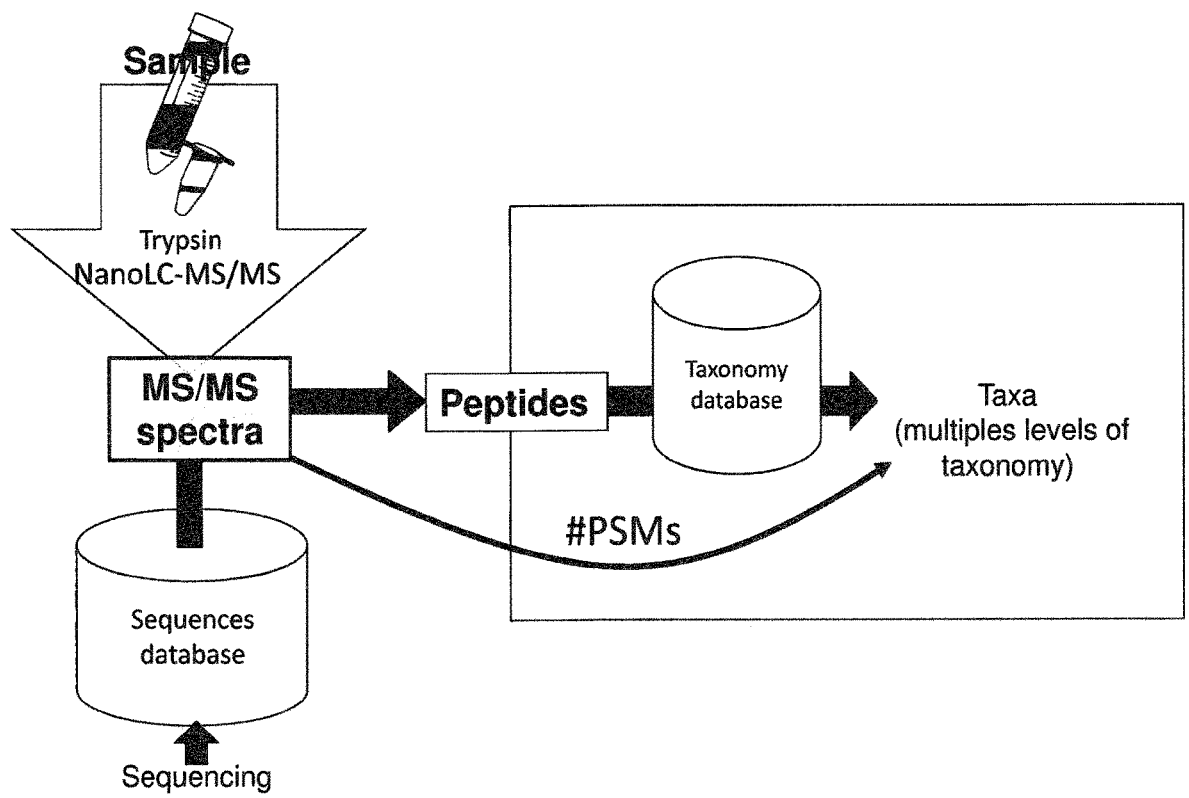

International Search Report and Written Opinion issued in corresponding International Patent Application No. PCT/IB2014/063560 dated Dec. 22, 2014.

* cited by examiner x < d : y = N * (A * exp(-d/a) + (1 - A) * exp(-d/b))
x >= d : y = N * (A * exp(-x/a) + (1 - A) * exp(-x/b))
■Taxon Escherichia coli K-12 (83333)
A=0.60 a=0.0008 b=0.0800 N=1146 d=0.0011
■Taxon Yersinia pestis KIM10+ (187410)
A=0.60 a=0.0008 b=0.0800 N=1256 d=0.0013
Fit result: $R^2 = 0.9953$ x < d : y = N * (A * exp(-d/a) + (1 - A) * exp(-d/b))
x >= d : y = N * (A * exp(-x/a) + (1 - A) * exp(-x/b))
■Taxon Sphingomonas wittichii RW1 (392499)
A=0.60 a=0.0008 b=0.0800 N=2834 d=0.0000
Fit result: $R^2$ = 0.2010 x < d : y = N * (A * exp(-d/a) + (1 - A) * exp(-d/b))
x >= d : y = N * (A * exp(-x/a) + (1 - A) * exp(-x/b))
■Taxon Sphingomonas wittichii RW1 (392499)
A=0.60 a=0.0008 b=0.0800 N=2610 d=0.0012
■Taxon Escherichia coli BL21(DE3) (469008)
A=0.60 a=0.0008 b=0.0800 N=1305 d=0.0011
■Taxon Ruegeria pomeroyi DSS-3 (246200)
A=0.60 a=0.0008 b=0.0800 N=780 d=0.0064
Fit result: $R^2$ = 0.9957

$x < d : y = N * (A * \exp(-d/a) + (1 - A) * \exp(-d/b))$
$x >= d : y = N * (A * \exp(-x/a) + (1 - A) * \exp(-x/b))$
■Taxon Sphingomonas wittichii (160791)
A=0.60 a=0.0010 b=0.0800 N=2808 d=0.0017
■Taxon Escherichia coli (562)
A=0.60 a=0.0010 b=0.0800 N=1277 d=0.0013
■Taxon Ruegeria pomeroyi (89184)
A=0.60 a=0.0010 b=0.0800 N=844 d=0.0130
Fit result: $R^2 = 0.9757$ $x < d : y = N * (A * \exp(-d/a) + (1 - A) * \exp(-d/b))$
$x >= d : y = N * (A * \exp(-x/a) + (1 - A) * \exp(-x/b))$
■Taxon Sphingomonas (13687)
A=0.60 a=0.0008 b=0.0800 N=3906 d=0.0082
■Taxon Escherichia (561)
A=0.60 a=0.0008 b=0.0800 N=1435 d=0.0012
■Taxon Ruegeria (97050)
A=0.60 a=0.0008 b=0.0800 N=675 d=0.0022
Fit result: $R^2 = 0.9636$

METHOD OF DECONVOLUTION OF MIXED MOLECULAR INFORMATION IN A COMPLEX SAMPLE TO IDENTIFY ORGANISM(S)

The present invention relates to a method to determine the identity (if already reported in a taxonomic database) or the identity of the closest related organism reported in a taxonomic database of one or more organisms present in a sample. The present invention does this by comparing a data set acquired by analysing at least one component of the biological sample for instance its protein content, and comparing this with a database derived from large programs of genome sequencing and annotation of known organisms so as to match each component of the protein content of the sample to one or more taxon and then collating the phylogenetic distance between the taxa and the number of matches.

The identification of microorganisms, viruses, multicellular organisms, or debris/contaminants originating from these organisms or culture media or additives in a sample is an important and ongoing area of research. The ability to identify the presence of known or emergent strains of infectious agents such as bacterial, viral or other disease causing organisms in a sample is important for the purposes of public health, epidemiology and public safety. Likewise being able to determine that a given product, such as a processed food or cosmetic preparation comprises only the claimed biological constituents is also a growing concern due to the increasing prevalence of highly processed food stuffs in the food chain and the reliance of consumers on manufacturers and retailers that their products can be trusted.

The routine and reliable identification of all the organisms present in a sample is still not routinely possible as existing methods generally rely upon the provision of reagents which are specific for a given organism or at best a related group of organisms. These reagents include materials such as 'organism specific' PCR primers or antibodies that can be used in a detection method. Other methods include DNA/RNA/antibody microarrays which comprise sequences from different organisms. In all cases due to the limitations of the number of materials comprised/used in such methods it is not possible to provide an entirely comprehensive assay. The problem with all these methods is therefore that identification is based upon the use of a specific detection reagent (or set of reagents).

More recently methods based upon analysing the complete or a part of the protein content of a sample have been developed using a mass spectrometry based method (U.S. Pat. No. 8,412,464). In this method the protein content of a sample is analysed using mass spectrometry, which leads to the detection of a number of peptide sequences which in turn are determined to arise from a certain organism or organisms and finally based upon a peptides-organisms assignment matrix a prediction is made about the organism present in the sample. The method relies upon the use of a curated database of bacterial sequences to ensure the veracity of the predictions and therefore is still restricted and cannot identify the presence of any organisms which has previously been characterized, but only those present in the curated database.

Moreover, the assignment matrix is difficult to apply to mixtures of organisms because of the numerous peptides shared between organisms which hinder the clustering methods used. A different approach has been applied to mixtures (Jabbour et al. 2010). It relies on the sum of peptides uniquely assigned to a specific organism to identify each component of a mixture. However, this last method suffers from the increasing density of sequenced genomes, which tends to dramatically lower the number of specific peptides, especially at the strain and species taxonomical levels. An example is given in table III column "# specific MS/MS", where the number of specific peptides is zero at the strain level and 15 at the species level but regularly lowered upon NCBI nr updates. In addition, the number of specific peptides or even the total number of peptides are not representative of the quantities of each organism because of "degenerate" peptides shared by organisms which must be specifically analysed in case of mixtures of organisms and contaminated samples.

The present invention relates to a method which allows the identification of any organism(s) present in a complex biological sample, by analysing the data in a more global and complete manner than any existing method. This new method compares data obtained on at least one component of the sample for instance its DNA, RNA, protein or lipid content, or upon a combination of data about these components, and based upon a comparison of this data set with existing databases allows the determination of the organism or organisms present in the sample if these are present in the database, or alternatively provides an accurate prediction of the relatedness of the unknown organisms present in the sample to the most closely related organism in the database. In addition this method allows for the quantification of the amount of each organism present in a sample. This quantification can either be relative, in terms of the percentage of each organism present or absolute. The claimed invention also allows an identification confidence level to be determined at each taxonomical level for each organism identified in the sample.

The claimed invention allows an identification of the organism or a part of the said organism present in a given sample without the need of fastidious isolation or cultivation of this organism.

The present invention can be used in a large number of fields including but not limited to microbiology, environmental sciences, food industry, farming, bioremediation, waste management, human health, green energy and green chemistry, biomining, cleaning controls, air and water quality management, plant and crop improvement, biodiversity management, counter-bioterrorism, forensics science, synthetic biology.

In accordance with the present invention there is provided a method to identify the organism(s) in a sample comprising the steps:

a) the generation or obtention of a data set assignable to one component of said sample, said component being selected among the group comprising peptide sequences and nucleic acid sequences;

b) the comparison of said data set with a database of known data concerning said component and the matching of each member of said data set to one or more taxon(s);

c) the calculation or assignment of the phylogenetic distance between each of said taxon(s) and the taxon k with the highest number of matches in said data set;

d) generation of a signature function for said taxon k, modelling the number of matches per taxon (Y axis) due to taxon k for each taxon at said phylogenetic distance from taxon k (X axis);

e) definition of an objective function selected from the group comprising sum of the squares of errors, maximum of errors and sum of absolute errors, said errors being calculated by subtraction of the signature function relating to the identified taxon k from the Y values assigned at step b) to each taxon;

f) minimization of the objective function by fitting the signature function parameters for taxon k, and comparison of the objective function with a threshold;

wherein:

(i) if said objective function is below the threshold at step f) and said signature function intersects the Y axis with a negative slope, said sample comprises the organism represented by said taxon with the highest number of matches;

(ii) if said objective function is below the threshold at step f) and said signature function intersects the Y axis with a zero slope, said sample comprises an unknown organism which is distant from said taxon k by the abscissa value of the point of the signature function where the slope becomes negative; and (iii) if said objective function is above the threshold at step f), said sample comprises at least one other detectable organism.

The above method enables to assess the presence and identity of at least one organism in a sample based upon analysing a data set generated from the peptide or nucleotide contents of the sample in the form of peptide or nucleotide sequence data. As the organisms present in the sample are unknown, the data would in general be generated in step a) with techniques such as mass spectrometry or NGS. In case of mass spectrometry, the data set hence consists of a set of spectra, and via NGS, the resulting data set consists of a large number of very short sequences. In any case, the obtained data do not allow a definitive match to be made as would be the case if a larger sequence could be established and matched to one entry in the public sequence databases. Such an approach allows a complete sampling of the genome/proteome to be made however, increasing the resolution of the claimed method. It is also possible that sequence data have already been generated and therefore the present invention may also consist of analysing such a pre-prepared data set.

Step b) of the above method comprises two steps: in the first one (b1), the analysis based on the peptide/nucleotide sequences set attributes each data (such as MS/MS spectrum or NGS read) from the data set to previously sequenced peptide or nucleotide sequences that are present in public or private databases annotated with taxon information such as Uniprot/ENA, generating peptide-spectrum matches (PSMs) or sequence-reads matches (SRMs). In the second step (b2), each PSM or SRM or equivalent data attributed to a known sequence is matched to one or more taxa (a taxon could be a group of organisms, for instance prokaryotes or *Mycobacterium* spp.). This process generates "PSM matched to taxa" (noted "PSMMTs" in the present text) in the case of MS/MS spectra, or "SRM matched to taxa" (noted "SRMMTs") in the case of NGS reads. Also, a result of step b) is to attribute to each taxon of the database a Y value equal to the number of associated matches (PSMMTs or SRMMTs). A vector of Y values is hence obtained, each Y value being the number of PSMMT or SRMMT associated to each taxon.

In step c) the taxon k with the highest number of matches (PSMMTs or SRMMTs) is used as the starting point from which phylogenic distances are calculated to each of the other taxa that comprise matching data set members.

In step d), a "signature function" is generated. This function is defined as a function modeling the contribution of a given taxon k to the number of matches per taxon (PSMMT or SRMMT plotted on the Y axis) observed for any taxon, using the phylogenic distance between said taxon and taxon k (plotted on the X axis). Another way of describing step d) is as follows:

d) generation of a deconvolution function for said taxon k, based on a correlation curve between the number of matches per taxon (Y axis) and said phylogenetic distance (X axis).

In the above wording of step d), the correlation function is the generical function observed to best fit all available taxa data points plotted for several mono-organisms data sets, using for each taxon the phylogenetic distance from taxon k with the highest number of PSMMT/SRMMT (X-axis) and the number of PSMMT/SRMMT (Y-axis). The correlation curve is the correlation function with parameters values adjusted on specific mono-organisms data sets to improve the fit to the taxa data points for specific clades or taxonomical levels. The deconvolution function is based on a correlation curve to inherit parameters settings in a particular clade or level context, possibly in replacement of standard parameters settings.

In step f), in the cases (i) and (ii), taxon k is the sole organism present in the sample in a detectable amount.

The "signature function" is hence strictly identical to the "deconvolution function" pertaining to taxon k.

Deconvolution is a process that is used to reverse the effects of convolution on data. Convolution is a mathematical operation on at least two functions, that produces a third function. This convolution can make the analysis/use of the data in one or both of the original functions difficult or impossible and therefore deconvolution allows the recovery of the original function(s) from their convoluted form. In the present context, a convolution is a linear combination of signature functions where each $N_k$ value is the contribution of each taxon k in the overall signal.

In the present invention the deconvolution is the determination of the set of signature functions, corresponding to a set of taxa k, which best matches the Y vector calculated in step b) by the sum of $Y_k$ vectors (one value per taxon) modelled by the signature functions.

In the above method, the Y vector is matched to the signature function corresponding to taxon k with the highest number of PSMMT (or SRMMT). The signature function parameters are fitted to minimize an objective function selected from the group comprising the sum of the squares of the errors, maximum of errors and sum of absolute errors, said error being calculated by subtraction of the signature function relating to the identified taxon k from the Y values assigned at step b) to each taxon; iterations of the method can then be performed by repeating steps c) to f) of the method, wherein:

in step c), the "taxon k with the highest number of matches in said data set" is substituted with the taxon $k_p$ (wherein p is the number of iterations) with the highest positive error or the taxon with a number of specific matches;

in step d), "taxon k" is replaced by "taxon $k_p$";

in step e), "calculated by subtraction of the signature function relating to the identified taxon k" is replaced by "calculated by subtraction of the sum of the signature functions relating to the identified taxa k to $k_p$" and in step d), "taxon k" is replaced by "taxon $k_p$", until the objective function value in step e) is below the threshold, or until the objective function output change upon repetition is below a second threshold.

If one taxon k is sufficient to model the Y vector, and if the signature function fitted intersects the Y axis with a negative slope or gradient, then one can affirm that the organism present in the sample is the taxon with the highest number of matches. In contrast, the methods disclosed in the prior art, such as the method disclosed by J. P. Dworzanski et al. (Journal of proteome research, 2006) only identify the organism which has the highest number of sequences and not spectra (PSMMTs), i.e., it only identifies the taxon present in the database which is the closest to the organism present in the sample. However, by performing the method of Dworzanski et al., one cannot determine if the organism which has the highest number of matches is really present in the sample, or if the organism present in the sample is not referenced in the database used. To the contrary, when performing the method according to the present invention, the presence of an unknown organism (i.e., one from which sequence data has not previously been generated and that is not present in the database(s) used) is clearly revealed by the fact that the fitted signature function intersects with the Y axis with no slope or gradient. Said unknown organism is then separated from the organism of the taxon with the highest number of matches by the phylogenic distance previously calculated as separating the taxon with the highest number of matches and the first taxon plotted on the graph which is intersected with a negative slope or gradient. In other words, the phylogenetic distance between the unknown organism and the taxon with the highest number of matches is the abscissa value of the point of the signature function where the slope becomes negative.

The matching of the sequences from the sample to taxa is performed by comparing each of these sequences to sequences present in public and/or private sequence databases in which sequences are annotated with taxon information, using techniques such as BLAST. This leads to a list of taxa (which may be any taxonomical grouping) and these are sorted in order of the number of matching sequences they comprise.

In step d), the generation of the signature function is the fitting of the function parameters to best match the $Y_k$ vector, i.e., the modelled number of matches per taxon, to the Y vector, using the phylogenic distance between each taxon and the taxon k with the highest number of matches to model each $Y_k$ vector value. A plot of taxon data points with number of matches on the Y axis and distances on the X axis and of corresponding modelled $Y_k$ values shows the fit quality, assessed using the objective function.

As indicated above, the determination of whether or not the organism identified in the sample is known or unknown (this means it has previously been sequenced and is present in the sequence database or not) is established based upon whether the signature function calculated and plotted in step d) intersects with the Y axis as a plateau or a slope, that is whether the gradient of the function is equal to 0 or not. In the case of a plateau (gradient=0) the organism is unknown and in the case of a slope (gradient≠0) the organism is the organism of the taxon that has the highest number of matches.

This method can be applied to the analysis of a sample using any method that generates signals that can be assigned to taxonomical levels (strain, species, genus, etc.); the analysis could therefore be upon aspects of the sample such as the entirety or a part of its protein content (global molecular weights or sequences or subset of sequences), peptide content (global molecular weights or sequences), lipid profile, metabolite profile or nucleotide content (size of fragments or sequences or subset of sequences). The assignment of the signal to a taxonomical level can be done either by interpretation of the signal (or part of it) or correspondence (or partial correspondence) with records established previously or predicted for individual organisms.

The data set can be generated using methods and materials such as liquid chromatography, mass spectrometry, liquid chromatography/mass spectrometry, static fluorescence, dynamic fluorescence, high performance liquid chromatography, ultra-high performance liquid chromatography, enzyme-linked immunoadsorbant assay, real-time PCR, or combinations thereof and wherein said mass spectrometry is liquid chromatography/mass spectrometry, liquid chromatography/mass spectrometry/mass spectrometry, ultra-high performance liquid chromatography mass spectrometry/mass spectrometry, Matrix-assisted laser desorption/ionization (MALDI) mass spectrometry/mass spectrometry, Biological Aerosol Mass Spectrometry, ion mobility/mass spectrometry or ion mobility/mass spectrometry/mass spectrometry, the tandem mass spectrometry being performed in data dependent mode or data independent mode, RNA or DNA microarrays; RNA or DNA or protein sequencing methods, protein arrays; high-throughput antibodies arrays, or a combination of any of these. These various methods can be performed in a data dependent or data independent fashion.

In accordance with a preferred further embodiment of the present invention multiple components of the sample are analysed, for instance the DNA or protein content is analysed using appropriate techniques.

In accordance with the present invention the sample comprises eukaryotic organisms, animals, bacteria, archaea, spores, protista, algaea, plants, virus, viral capsids, fungi, yeasts, eukaryotic cells, blood cells, cancer cells, neuronal cells, primary cells or epithelial cells, or parts or mixture of these items such as plant roots, plant leafs, plant seeds, animal tissues, animal organs, or derived cells such as those obtained by repeated cultures under selective or non-selective pressure, or engineered cells such as genetically modified organisms or organisms created by means of synthetic biology, or parts secreted or released by these items such as milk, toxins, enzymes, antibiotic resistances, virulence factors, growth factors or hormones, or parts considered as contaminants such as keratins or unexpected molecules, or parts considered as additives such as molecules used as decoy or used as standards or as culture medium components.

In accordance with the present invention "taxon" means a group of one (or more) populations of organism(s), which a taxonomist adjudges to be a unit.

In accordance with the present invention "peptide spectrum match(es)" or "PSM(s)" means a match from a MS/MS spectrum query to a given peptide. "PSM matched to taxa" or "PSMMTs" means a match from a PSM to a taxon.

In accordance with the present invention "nucleic acid sequence" means the sequence of a deoxyribonucleic acid (DNA) or ribonucleic acid (RNA), or part of this sequence.

In accordance with the present invention and except when the context renders evident that it refers to the quantification method called "selected reaction monitoring", "SRM(s)" refer to "sequence reads match(es)" and means a match from a read by next generation sequencing (NGS) to a taxon. "SRM matched to taxa" or "SRMMTs" means a match from a SRM to a taxon.

In accordance with the present invention "nucleic acid sequence reads" means the output of any method or technology that is used to determine the order of the bases (adenine, guanine, cytosine, thymine, uracile) in a strand of DNA or RNA or the output of any method or technology that is used to assemble parts of deoxyribonucleic acid (DNA) or ribonucleic acid (RNA) sequences.

In accordance with the present invention "nucleic acid sequence reads quality factor" means the global evaluation of per-base error probabilities reported by sequencers for each nucleic acid sequence reads (mean per-base error probabilities reported for each nucleotide position of the sequence; cumulated per-base error probabilities for all the nucleotides).

In accordance with the present invention "nucleic acid sequence quality factor" means the global evaluation of per-contig error probabilities for the assembly result.

In accordance with the present invention "nucleic acid sequence reads redundancy" means the number of identical nucleic acid sequence reads.

In accordance with the present invention "specific matches" means components that are assigned at a unique taxon at a given taxonomic level.

In accordance with the present invention there is provided a method wherein the said component is a peptide sequence, said matches are peptide spectrum matches and the generation of data set in step a) is performed by tandem mass spectrometry. As indicated above, each of the spectra is attributed to one or more database sequences and hence assigned to a taxon with the total number of matches per taxon being recorded. Once all the spectra from the sample have been matched, the taxon with the most matches is identified.

In accordance with a further aspect of the present invention there is provided a method to identify the organism(s) in a sample comprising the steps:

a) the generation of a data set comprising a plurality of peptide spectrum matches from said sample by mass spectrometry;

b) comparison of said data set with a database of known proteins and the assignment of each of said plurality of peptide spectrum matches to one or more taxon(s); calculation of the number of peptide spectrum matches matching each taxon is preferably performed in this step;

c) calculation or assignment of the phylogenetic distance between each of said taxon(s) and taxon k with the highest number of peptide spectrum matches;

d) generation of a signature function for said taxon k modelling the number of peptide spectrum matches per taxon (Y axis) for each taxon at said phylogenetic distance from k (X axis);

e) definition of an objective function selected from the group comprising sum of the squares of errors, maximum of errors and sum of absolute errors, said error being calculated by subtraction of the signature function relating to the identified taxon k from the Y values assigned at step b) to each taxon;

f) minimization of the objective function by fitting the signature function parameters for taxon k, and comparison of the objective function with a threshold;

wherein:

(i) if said objective function is below the threshold at step f) and said signature function intersects the Y axis with a negative slope, said sample comprises the organism represented by said taxon with the highest number of matches;

(ii) if said objective function is below the threshold at step f) and said signature function intersects the Y axis with a zero slope, said sample comprises an unknown organism which is distant from said taxon k by the abscissa value of the point of the signature function where the slope becomes negative; and (iii) if said objective function is above the threshold at step f), said sample comprises at least one other detectable organism.

In accordance with the present invention the term "taxon" may mean a superkingdom, phylum, class, order, family, genus, species, strain or any other recognised group or population of organisms which are phylogenetically related and which have characters in common which differentiate the group from other such groups.

In accordance with the present invention the correlation curve used to generate a deconvolution function in step d) is a monotonic decreasing function (as well as the signature function).

In accordance with the present invention the phylogenetic distance may be calculated as described in the examples below based upon the relatedness of the taxa selected during step b) of the claimed method or the phylogenetic distance may be assigned to each taxon on the basis of an existing measurement of the relatedness of the taxa such as those described in the art.

In accordance with a further aspect of the present invention said taxa are clades at a given taxonomical level, ranging from superkingdom to species, or to the most precise taxonomical rank beyond the species level such as subspecies. Peptide spectrum matches per taxon are then the aggregation of subtaxa data. Distances between taxa are infered from distances between sub-taxa, using for example mean or median calculation.

In accordance with a further aspect of the present invention, said database comprises only data which has been fully annotated and attributed. A number of whole shotgun sequenced genomes/proteomes etc, have not been fully analysed, for instance they lack cluster of orthologous group information. In accordance with this further aspect of the present invention, the database against which the data set of step a) is compared comprises only data that have been fully annotated and attributed, that has been shown to represent a native structure/sequence/profile from the organism which was sequenced/analysed. In accordance with this aspect of the present invention, step b) may be performed using a first database comprising all selected data and a second database comprising only annotated and attributed data. In accordance with this aspect of the present invention if the taxon with the most matches based upon the second database is different to the taxon with the most matches based upon the first database, the taxon selected on the basis of the second database is chosen.

In accordance with the present invention, the signature function in step d) has the formula:

$$0 \leq X_k < d_k : Y_k = N_k \times (A_k \times \exp(-d_k/d1_k) + (1-A_k) \times \exp(-d_k/d2_k))$$

$$d_k \leq X_k : Y_k = N_k \times (A_k \times \exp(-X_k/d1_k) + (1-A_k) \times \exp(-X_k/d2_k)).$$
Formulae 1 wherein $Y_k$ is the number of matches due to taxon k attributed to taxa data points, exp( ) is the exponential function, $N_k$ is the number of matches attributed to the taxon k chosen as the reference for distances calculation (X-axis), $X_k$ is the phylogenetic distance between a taxon and taxon k, $A_k$ is the percentage of the exponential term in the form $\exp(-X_k/d1_k)$, with the complement to 1 attributed to the second exponential term in the form $\exp(-X_k/d2_k)$. Terms $d1_k$ and $d2_k$ are homogenous to distances representing components more or less shared between taxa due to sequence conservation. In practise, $d1_k$ and $d2_k$ have preset values. Their values are empirical and can be fitted or not during the minimization of the objective function described below. In examples 2.1 to 2.6 of the experimental part below, the values of $d1_k$ and $d2_k$ are 0.01 and 0.08, respectively; their values are indicated as "a" and "b" in the examples 2.9 and 2.10.

$d_k$ represents the phylogenetic distance between the taxon in the sample and the closest taxon in the database, which is said taxon k with the highest number of matches.

In accordance with the present invention, step f) of the above methods is preferably performed by fitting parameters, for each identified taxon k, selected from the group: $N_k$, $d_k$, $A_k$, $d1_k$ and $d2_k$.

This method can be performed sequentially so that if more than one organism is present in the sample, once a first organism has been identified the modelled matches for the identified taxon can be removed (alternatively the data set is re-evaluated in terms of matches for each identified taxon at each iteration) from the data set and the steps listed above performed again. This can be repeated until all organisms present are identified.

In accordance with this further aspect of the present invention, the claimed method may be used to identify several (possibly all of the) organisms present in a sample, by identifying each organism present therein by subtracting the data present in the data set which relates to each identified organism either iteratively or concurrently until only data at or below noise level remains.

An important aspect of the present invention is hence a method of identifying several organisms in a sample, comprising performing the method described above and then repeating steps c) to f) at least once, wherein the taxon with the highest number of matches in said data set in step c) is substituted with the taxon with the highest positive error or the taxon with a number of specific matches, said error being defined in step f), until the objective function value is below a first threshold or the objective function output change upon repetition is below a second threshold.

Another way of defining this method is a method of identifying several organisms in a sample, comprising performing the steps a) to f) and then repeating the following steps $c_p$) to $f_p$), wherein p is the number of iterations:

$c_p$) the calculation or assignment of the phylogenetic distance between each of said taxon(s) and the taxon $k_p$ with the highest positive error or the taxon with a number of specific matches;

$d_p$) generation of a signature function for said taxon $k_p$, modelling the number of matches per taxon (Y axis) at said phylogenetic distance between said taxon and taxon $k_p$ (X axis);

$e_p$) definition of an objective function selected from the group comprising sum of the squares of errors, maximum of errors and sum of absolute errors, said errors being calculated by subtraction of the sum of the signature functions relating to the identified taxa k to $k_p$ from the Y values assigned at step b) to each taxon;

$f_p$) minimization of the objective function by fitting the signature function parameters for taxa k to $k_p$, and comparison of the objective function value with a first threshold and/or and comparison of the objective function change upon repetition with a second threshold, wherein:

(i) if said objective function is below the first threshold or the objective function change is below the second threshold at step $f_p$), said sample comprises the organisms at distances $d_k$ to $d_{kp}$ from said taxons k to $k_p$, with corresponding number of matches $N_k$ to $N_{kp}$, wherein $d_k$ and $N_k$ are the parameters for the signature function defined above pertaining to taxon k (the first identified taxon), and $d_{kp}$ and $N_{kp}$ are the parameters for the signature functions corresponding to taxa $k_p$ from the subsequent iterations, wherein all parameters have values obtained in the last iteration.

(ii) if said objective function is above the first threshold or the objective function change is above the second threshold, said sample comprises at least one other detectable organism, necessitating another iteration to identify all the organisms detectable in the sample.

In accordance with a preferred embodiment of the claimed invention, step b) is performed iteratively on an increasingly lower number of taxa, wherein only the identified taxa after repetition of steps c) to f) are retained and then from within these retained taxon(s) a new comparison of the data set with a database of known proteins is made and the assignment of each of said plurality of peptide spectrum matches to one or more higher taxon(s).

In accordance with the present invention, step b) is performed iteratively on an increasingly smaller number of taxa, wherein only the taxa identified after repetition of steps c) to f) are retained and then from within these retained taxon(s) further steps b) to f) are repeated at least one time.

In accordance with the present invention, step b) is performed iteratively on an increasingly smaller number of taxa, wherein only the taxa with the highest numbers of specific matches are retained and then from within these retained taxon(s), further step b) to f) are repeated at least one time.

In accordance with a further aspect of the present invention there is provided a method to quantify the organism(s) in a sample after their identification comprising the steps:

a) the steps of the identification method according to the present invention, wherein each group of organisms present in said sample are assigned to a taxon;

b) the substitution of each assigned match within said taxon(s) by a measurement of the component associated with the match in the sample;

c) the ordering of the quantified matches from step b) by quantity, from highest to lowest and the selection of a subset;

d) the calculation of a taxon quantification based on the selected subset, using the sum, or mean, or median of said subset.

In accordance with this aspect of the present invention in step b) the measurement of peptide abundance is performed by a method selected from the group comprising a method using eXtracted Ion Chromatograms, a quantification method based on mass spectrometry data or associated liquid-chromatography data, the MS/MS total ion current and methods based on peptide fragments isolation and quantification such as selected reaction monitoring (SRM), multiple reaction monitoring (MRM) or parallel reaction monitoring (PRM).

In accordance with this aspect of the present invention in step b) the measurement of nucleotide abundancy is performed using "nucleic acid reads" quality factor or "nucleic acid reads" redundancy.

In accordance with the present invention in step c) the top 100 or top 10 peptide sequence matches are selected.

In accordance with a further aspect of the present invention the said component is a nucleic acid sequence, said matches are nucleic acid sequences, and wherein in step b) the measurement is performed using "nucleic acid" quality factor.

In accordance with a further aspect of the present invention the said component is a nucleic acid sequence, said matches are "nucleic acid sequence reads", and wherein in step b) the measurement is performed using "nucleic acid reads" quality factor or "nucleic acid reads" redundancy.

FIG. 1: shows a Schematic of the PSM-to-taxon inference process.

Figure 2:
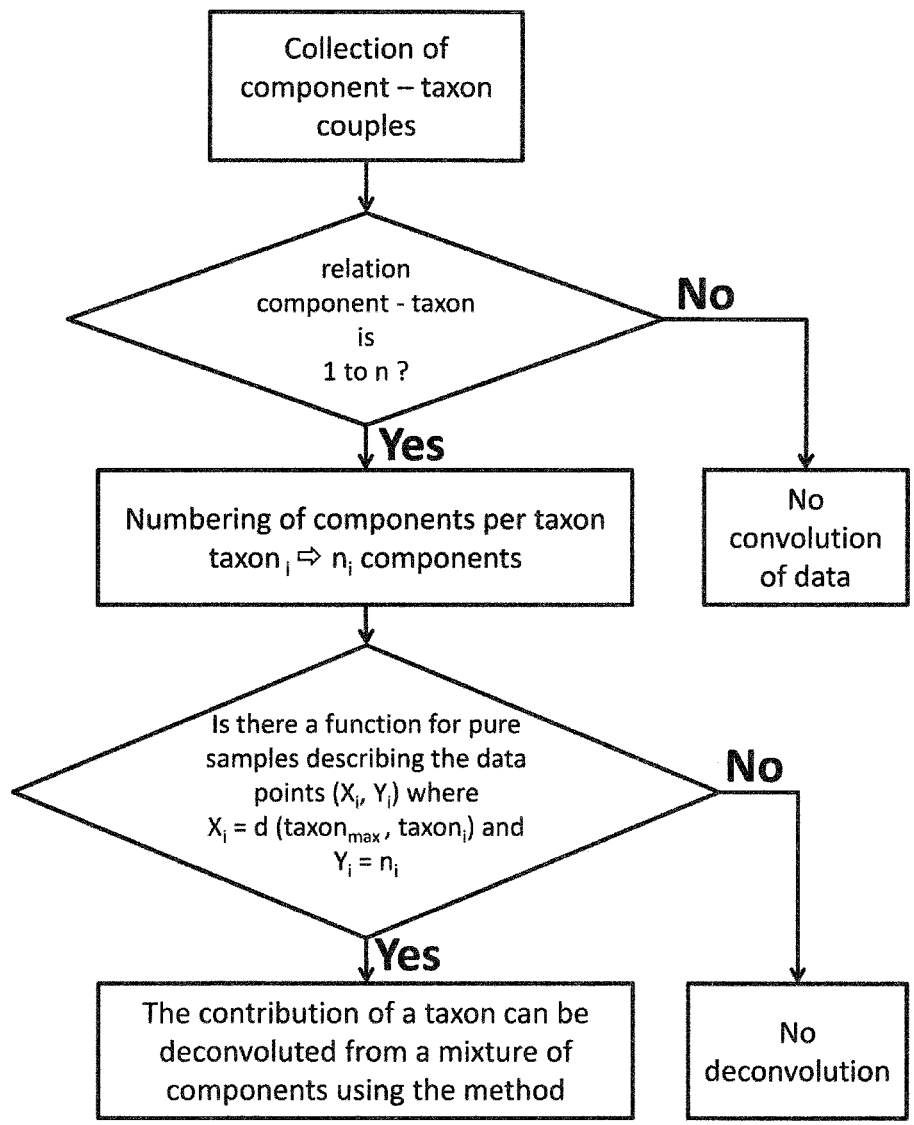
Figure 7:
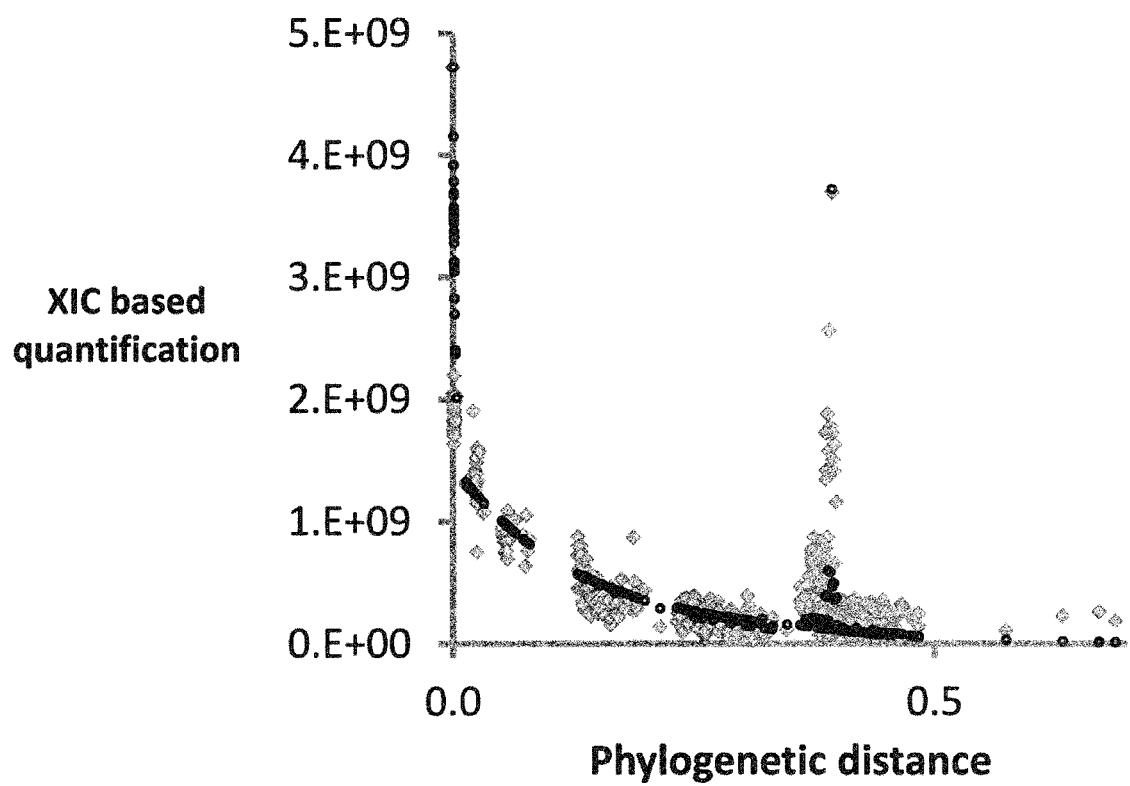

FIG. 2: Workflow for the evaluation of fields where the deconvolution process can be applied. The first stage, collection of component—taxon couples, corresponds to FIG. 1 in the case of mass spectrometry data, or the BLAST analysis process for raw read data for the DNA sequencing example. The second stage identifies if the data is convoluted in terms of taxonomical assignment. All molecular sequences too short to be organism-specific are also taken into account (for example peptides or short shotgun nucleic acid sequencing reads). After a counting stage, the evaluation of data points representing counts in function of a phylogenetic distance is evaluated. If a phylogenetic distance can be found that allows a proper function fit of the data, then the invention can be applied. As shown in FIG. 3A, it is the case with tandem mass spectrometry data acquired on peptides. FIG. 7 shows that the same applies to shotgun sequencing reads acquired during a nucleic acid sequencing project.

Figure 3:
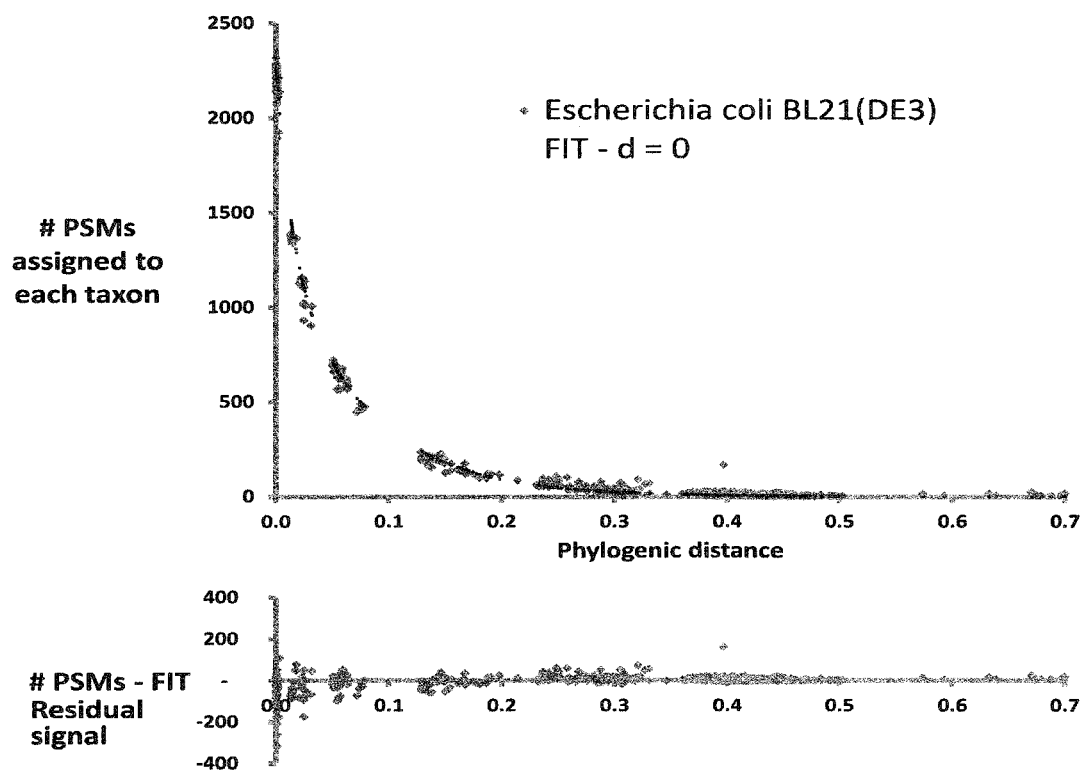

FIG. 3: Analysis of a sample containing a pure bacterial organism, namely *Escherichia coli* BL21(DE3), at the lowest possible taxonomical rank. On the graph in the upper panel at the strain level (taxonomical "no rank" level for bacteria), each dot is representative of the number of PSMs attributed to a given taxon as a function of the distance calculated (using conserved cluster of orthologous groups (COGs)) between this taxon and the taxon with the highest number of associated Peptide-Spectrum Matches (PSMs). Markers for a correlation curve in the form $Y=N(A*e^{(-X/d1)}+(1-A)*e^{(-X/d2)})$ are plotted. The lack of data points consistently above the correlation curve markers (above zero for the residual signal) is indicative of a pure organism. The residual signal, i.e. difference between the experimental PSMs and the theoretical PSMs number given by the correlation, is plotted in the lower panel. As the slope is negative starting from the taxon where the highest number of PSMs has been detected, the identification result is this taxon.

Figure 4:
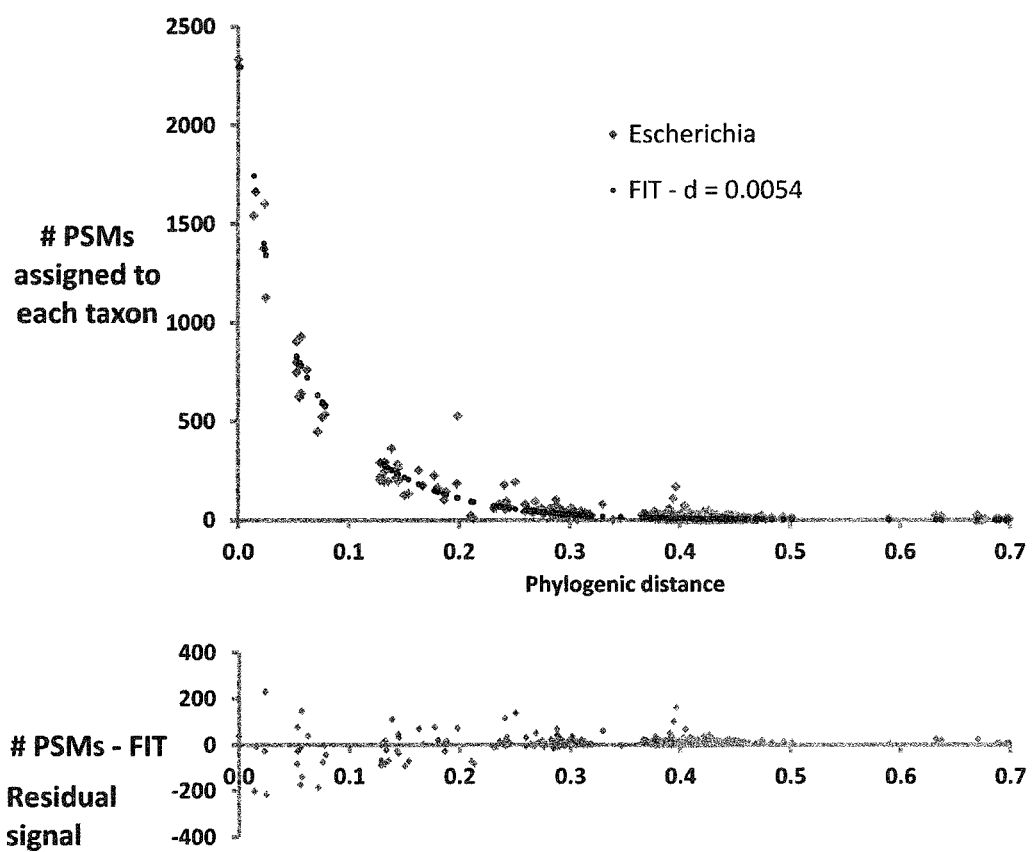

FIG. 4: Analysis of a sample containing a pure bacterial organism, namely *Escherichia coli* BL21(DE3), at the genus rank. On this graph at the genus level, each dot is representative of the number of PSMs attributed to a given taxon as a function of the distance calculated (using COGs) between this taxon and the taxon with the highest number of associated Peptide-Spectrum Matches (PSMs) as shown in the upper panel. A correlation curve in the form $Y=N(A*e^{(-X/d1)}+(1-A)*e^{(-X/d2)})$ is plotted. The residual signal is shown in the lower panel. The lack of data consistently above the correlation curve is indicative of a pure organism. As the slope is negative starting from the taxon where the highest number of PSMs has been detected, the identification result is this taxon.

Figure 5:
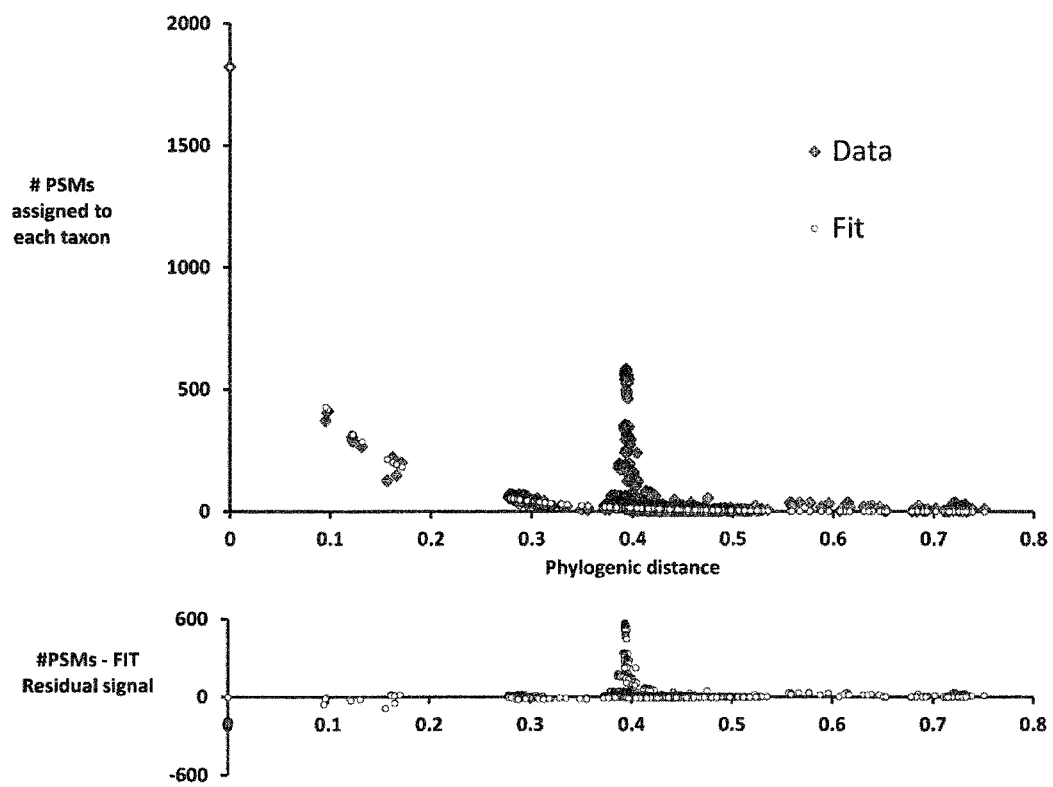

FIG. 5: Analysis of a sample containing a mixture of two bacterial organisms, *Escherichia coli* BL21(DE3) and *Ruegeria pomeroyi* DSS-3. On this graph at the strain level, each dot is representative of the number of PSMs attributed to a given taxon as a function of the distance calculated (using COGs) between this taxon and the taxon with the highest number of associated Peptide-Spectrum Matches (PSMs), in that case *R. pomeroyi* DSS-3 (taxid: 246200). A correlation curve in the form $Y=N(A*e^{(-X/d1)}+(1-A)*e^{(-X/d2)})$ is plotted, depicting the signal expected for a pure *R. pomeroyi* DSS-3 sample. The high and consistent positive residual signal at a phylogenetic distance of 0.4 unit from the *R. pomeroyi* DSS-3 taxon indicates that an additional organism is needed to fit the total signal. In this case, the residual signal is only due to the second bacteria present in the sample, namely *Escherichia coli* BL21(DE3) strain.

Figure 6:
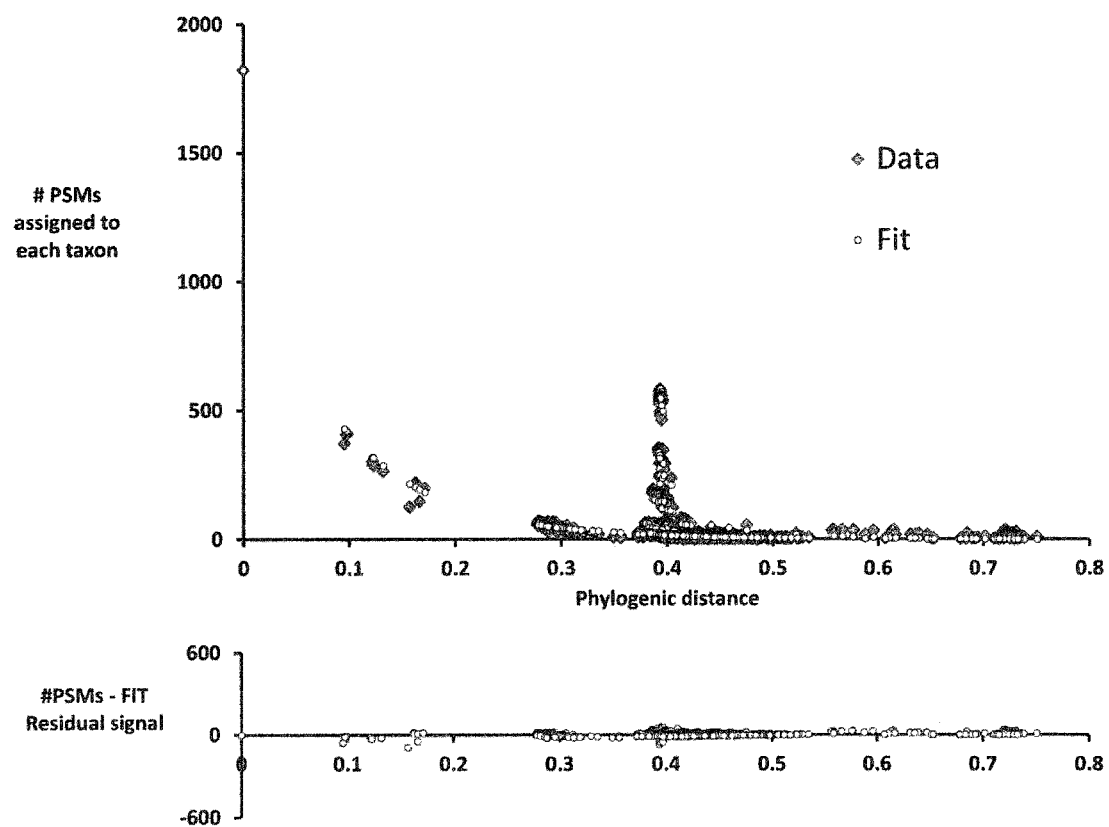

FIG. 6: The same data as in FIG. 5 is plotted, fitted with a mixture model of two components functions in the form $Y=N(A*e^{(-X/d1)}+(1-A)*e^{(-X/d2)})$, depicting the signal expected for a mixture of *Escherichia coli* BL21(DE3) and *Ruegeria pomeroyi* DSS-3. For each component, the X value used for fitting is relative to each reference organism, i.e., *E. coli* BL21(DE3) and *R. pomeroyi* DSS-3 respectively. However the graph displays for commodity both contributions on the same X axis. The lack of consistent positive residual signal indicates that the sample content is completely modelled and explained by a mixture of these two organisms.

FIG. 7: Example of the deconvolution method applied to quantify a mixture of two organisms, *Escherichia coli* BL21 and *Ruegeria pomeroyi* DSS-3, with equivalent cell amounts based on optical density measurements. The X-axis represents the distance of each taxon to *E. coli* BL21. The Y-axis corresponds to an eXtracted Ion Chromatogram (XIC) based quantification (intensity of the parent ion selected for fragmentation and as measured by the mass spectrometer and integrated along the chromatography) associated to each taxon. For each MS/MS spectrum, the m/z and retention time of the corresponding parent ion are used to extract a XIC value representative of a quantity. In this figure, the quantification of each taxon was based on the sum of the top 100 XIC intensities replacing the corresponding spectra. The results indicate top 100 XIC intensities of 3.75E9 and 4.8E9 for *R. pomeroyi* and *E. coli*, respectively; thus a ratio *R. pomeroyi/E. coli* roughly equivalent to 1:1.

Figure 8:
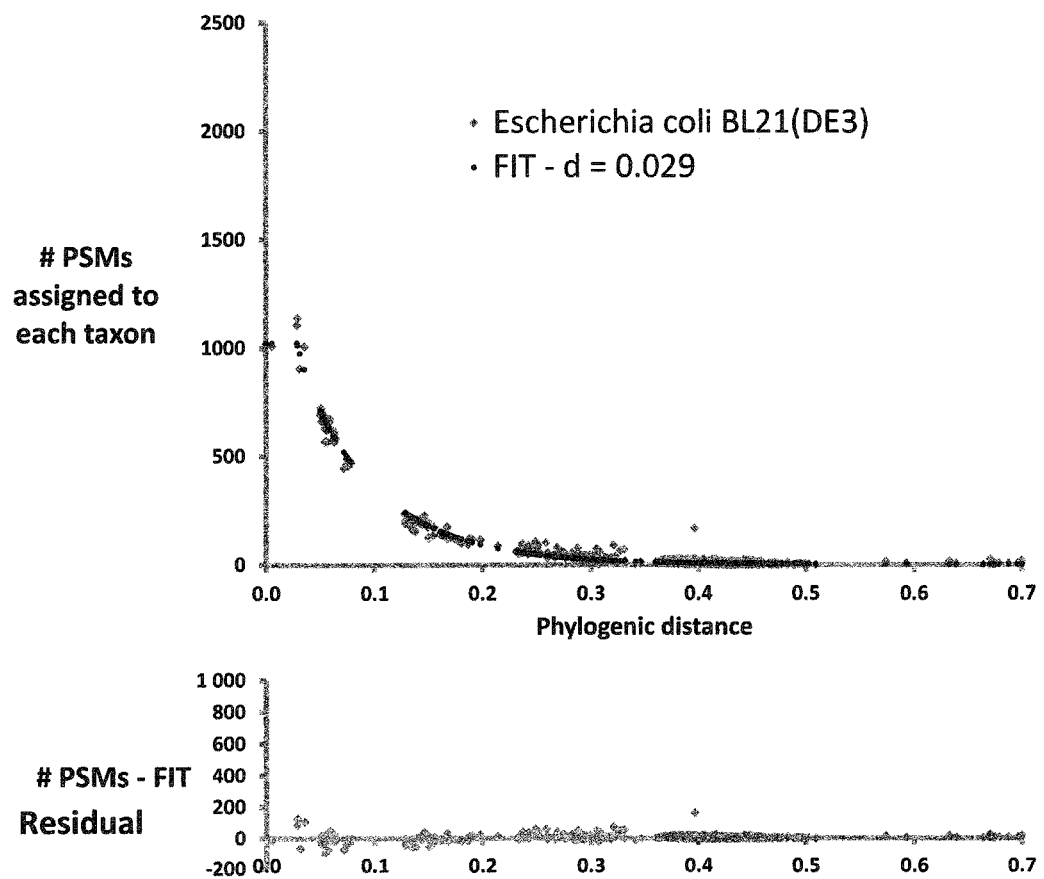

FIG. 8: Analysis of a sample containing a pure *E. coli* strain but not present in the database. Taxa closer than a distance of 0.025 have been removed from the search database mimicking the absence in the database of the closest-relative organisms. Curve fitting has been performed with function 2, with a leveling behavior over a distance of 0.029, indicative of the distance between the closest organism representative of the bacterial strain in the database and the strain present in the sample.

Figure 9:
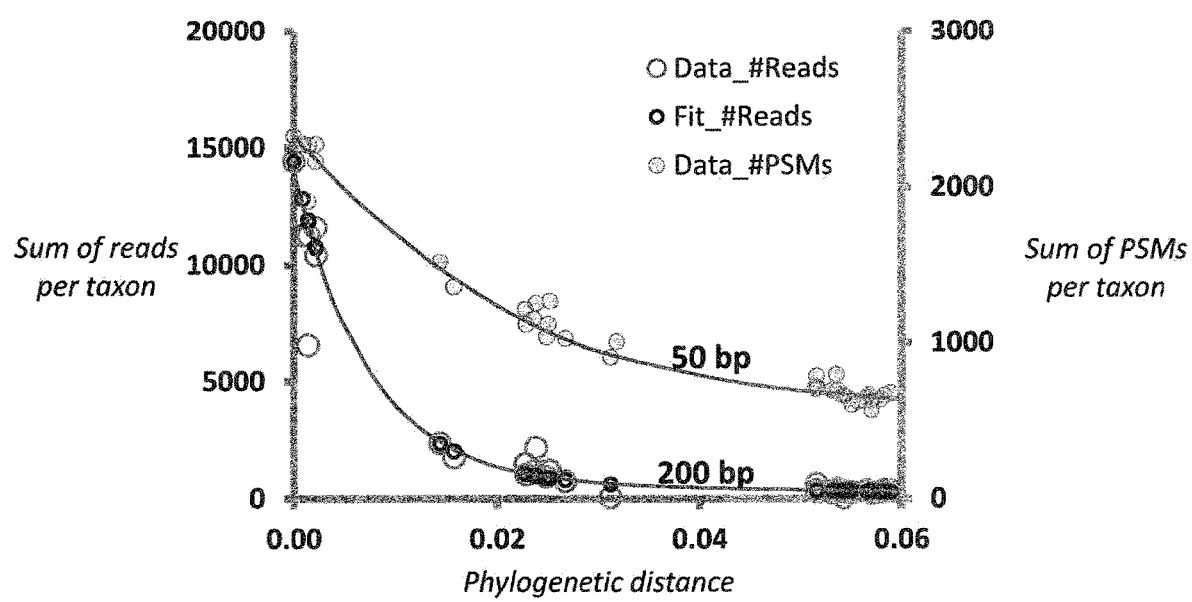

FIG. 9: Comparison of mass spectrometry-derived PSMs data and DNA sequencing results for a pure *Escherichia coli* sample at the species taxnomical level. Data points are taxa at the species level and their corresponding PSMs or DNA sequencing reads. The X-axis represents distances between the reference taxon (*Escherichia coli*) and all other taxa, calculated as previously described using the conserved COGs relationships. The left Y-axis represents the total number of DNA sequencing reads from an SRA subset associated to each taxon (see Table VI). The right Y-axis represents the total number of PSMs associated to each taxon as detailed previously. The mean peptide length for PSMs in this experiment is 16 residues, comparable to about a sequencing read of 50 bp. The SRA reads used were all 200 bp long, a length which corresponds to the current maximum read length for Illumina or Ion Torrent next-generation sequencing technologies. The figure shows that the results of deconvolution are comparable whatever the input data, i.e. peptide sequence established by tandem mass spectrometry or DNA sequencing reads, and point at the same taxon identification. As expected, a longer sequence read tends to give higher discrimination between closest relatives and increases the initial slope of the deconvoluted curve.

Figure 10:
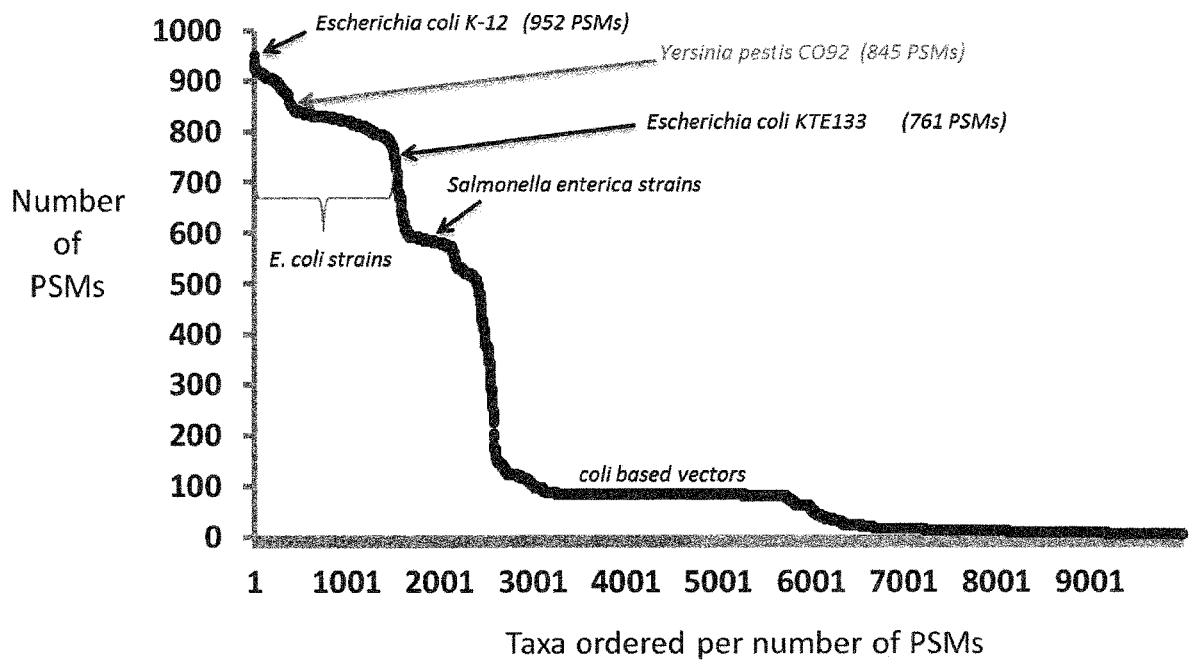

FIG. 10: Display of the first 10000 taxa at the most resolved taxonomical level, each taxon being represented by a dot. The horizontal axis is the index of the taxon, ordered by the number of associated spectra, and the vertical axis is the number of spectra per taxon attributed for the *E. coli* & *Y. pestis* mixture.

Figure 11:
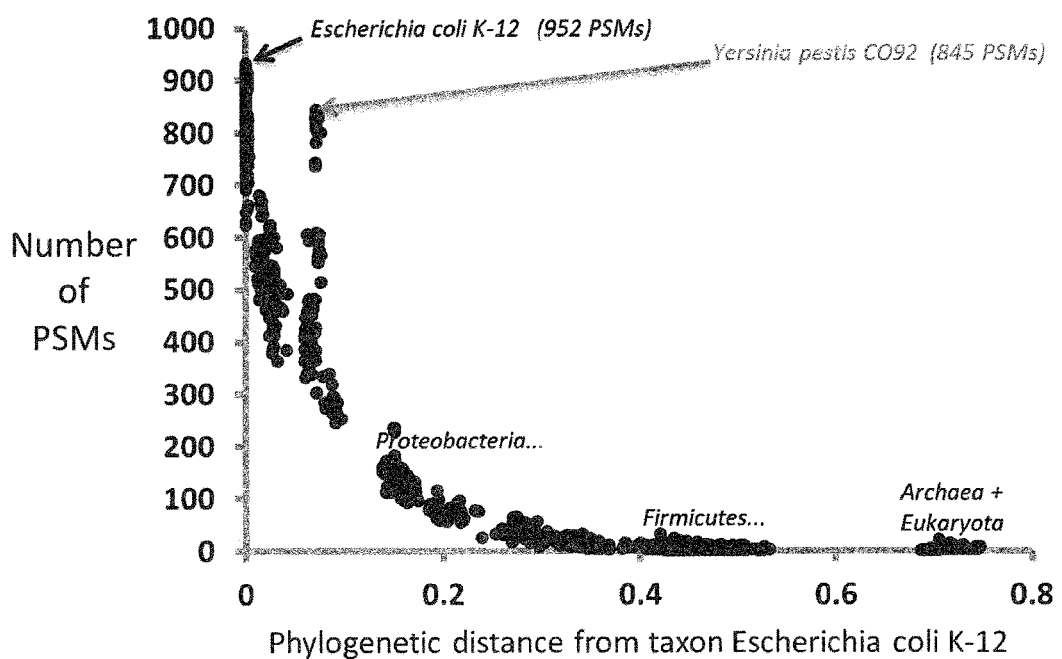

FIG. 11: Display of the same dataset as FIG. 10, with additional information associated to each taxa couple, which is a phylogenetic distance between these taxa. In this figure, the reference taxon used for the horizontal axis distance is *Escherichia coli* K-12 which is the taxon with the maximum number of associated PSMs. Each taxon is represented by a dot, which Y-axis value is the number of associated spectra as in FIG. 10.

Figure 12:
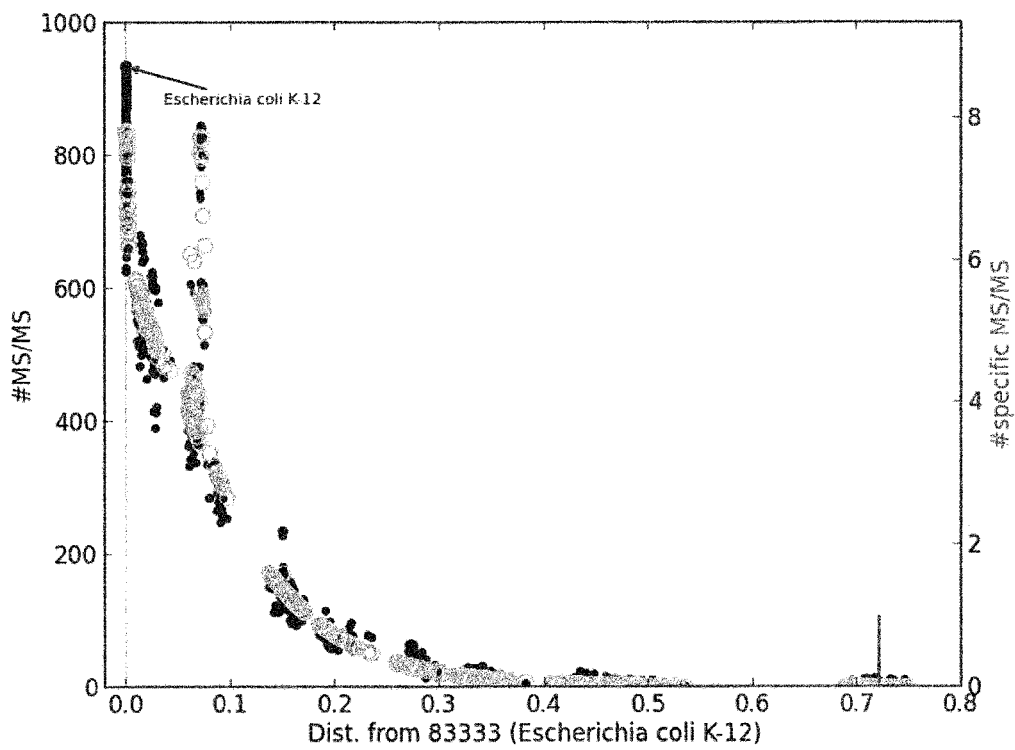

FIG. 12: Decomposition of the signal for the sample *Escherichia coli/Yersinia pestis* mixture with our method and resulting fitting parameters. Closed dark circles are taxa data points as in FIG. 2, open light grey circles are the fit results obtained by summation of the 2 signature functions with the parameters detailed below:

$$x<d: y=N^*(A^*\exp(-d/a)+(1-A)^*\exp(-d/b))$$

$$x>=d: y=N^*(A^*\exp(-x/a)+(1-A)^*\exp(-x/b))$$

■Taxon *Escherichia coli* K-12 (83333)
A=0.60 a=0.0008 b=0.0800 N=1146 d=0.0011
■Taxon *Yersinia pestis* KIM10+(187410)
A=0.60 a=0.0008 b=0.0800 N=1256 d=0.0013
Fit result: R^2=0.9953

Figure 13:
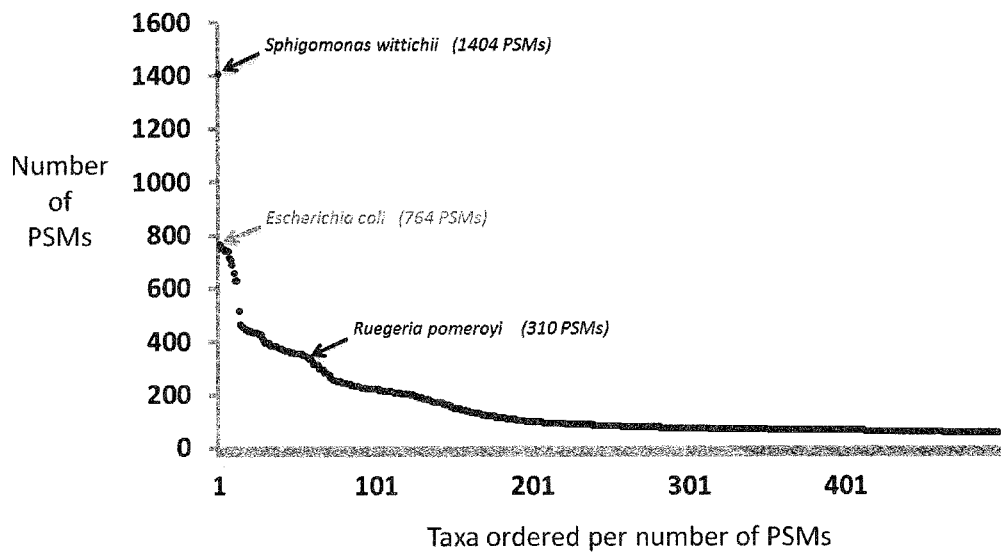

FIG. 13: Display of the first 500 taxa at the species taxonomical level, each taxon being represented by a dot. The horizontal axis is the index of the taxon, ordered by the number of associated spectra, and the vertical axis is the number of spectra per taxon attributed for the mixture.

Figure 14:
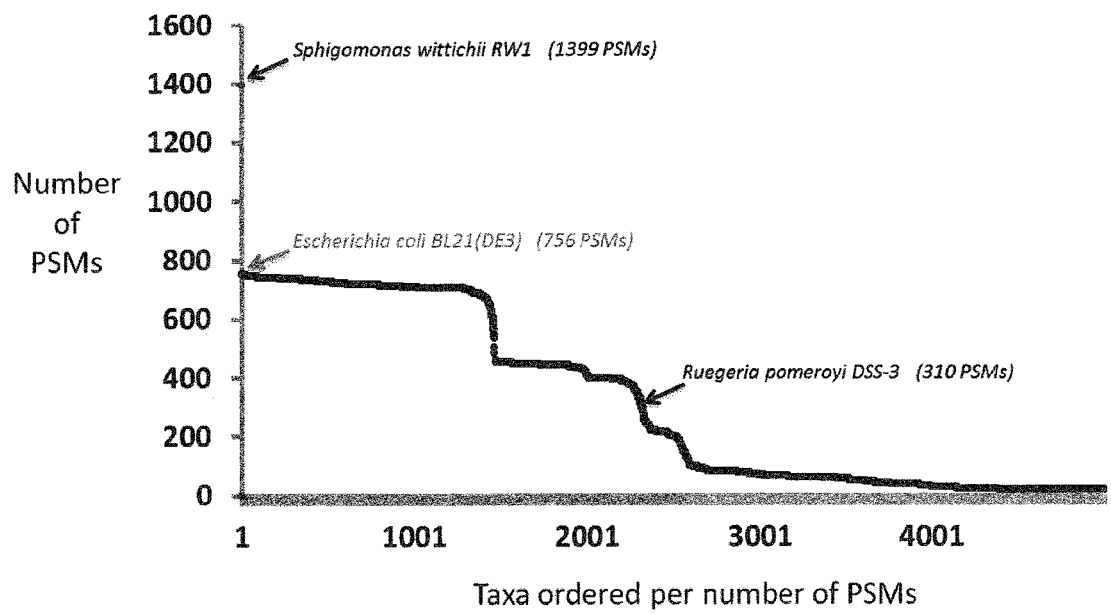

FIG. 14: Display of the first 5000 taxa at the most resolved taxonomical level, each taxon being represented by a dot. The horizontal axis is the index of the taxon, ordered by the number of associated spectra, and the vertical axis is the number of spectra per taxon attributed for the mixture.

Figure 15:
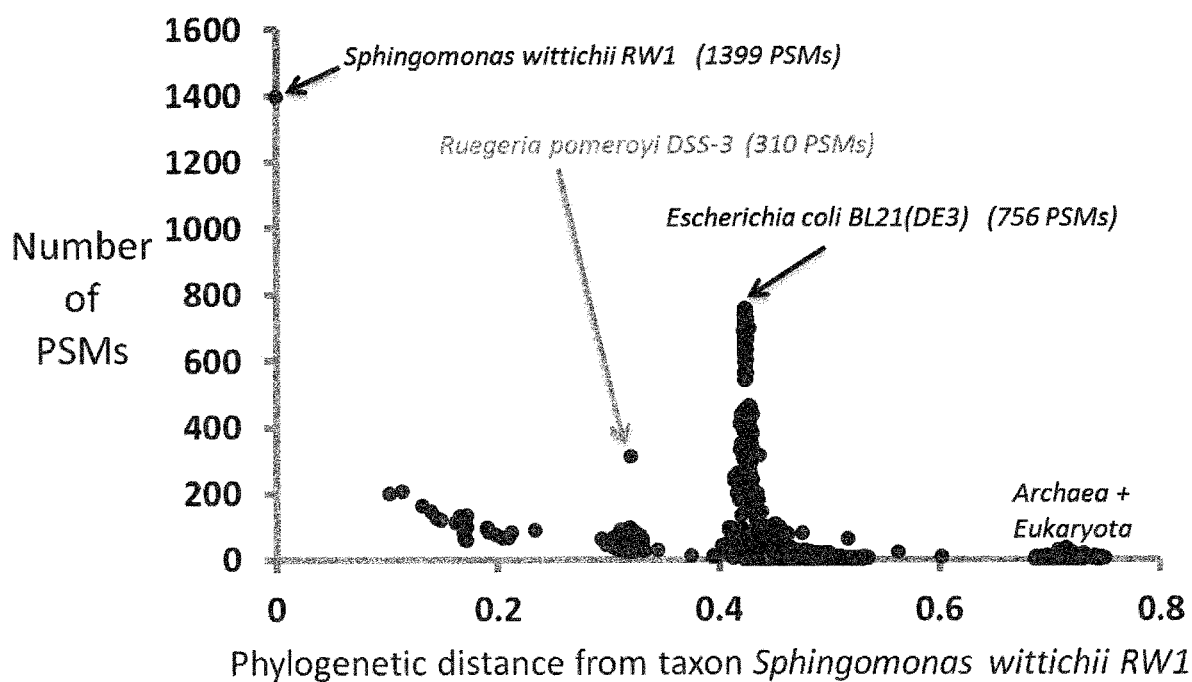

FIG. 15: Display of the same dataset as FIG. 14, with additional information associated to each taxa couple, which is a phylogenetic distance between these taxa. In this figure, the reference taxon used for the horizontal axis distance is *Sphingomonas wittichii* RW1, which is the taxon with the maximum number of associated PSMs. Each taxon is represented by a dot, which Y-axis value is the number of associated spectra as in FIG. 14.

Figure 16:
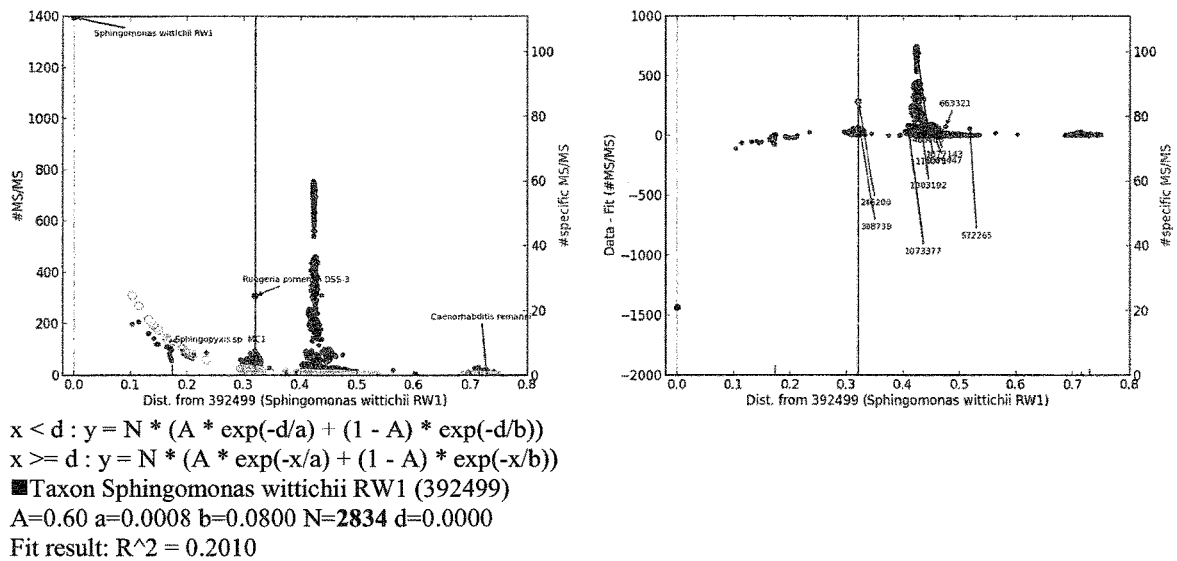

FIG. 16: Result of the first iteration for the sample *Sphingomonas wittichii/Escherichia coli/Ruegeria pomeroyi* mixture with our method at the most resolved taxonomical level. The left panel displays the fit obtained using only the signature signal for *S. wittichii* RW1, and on the right panel, the residual signal obtained by subtracting the fit to the data points is displayed. The next organism identified in the mixture is the data point with the maximum residual signal, namely *Escherichia coli* BL21(DE3).

$$x<d: y=N^*(A^*\exp(-d/a)+(1-A)^*\exp(-d/b))$$

$$x>=d: y=N^*(A^*\exp(-x/a)+(1-A)^*\exp(-x/b))$$

■Taxon *Sphingomonas wittichii* RW1 (392499)
A=0.60 a=0.0008 b=0.0800 N=2834 d=0.0000
Fit result: R^2=0.2010

Figure 17:
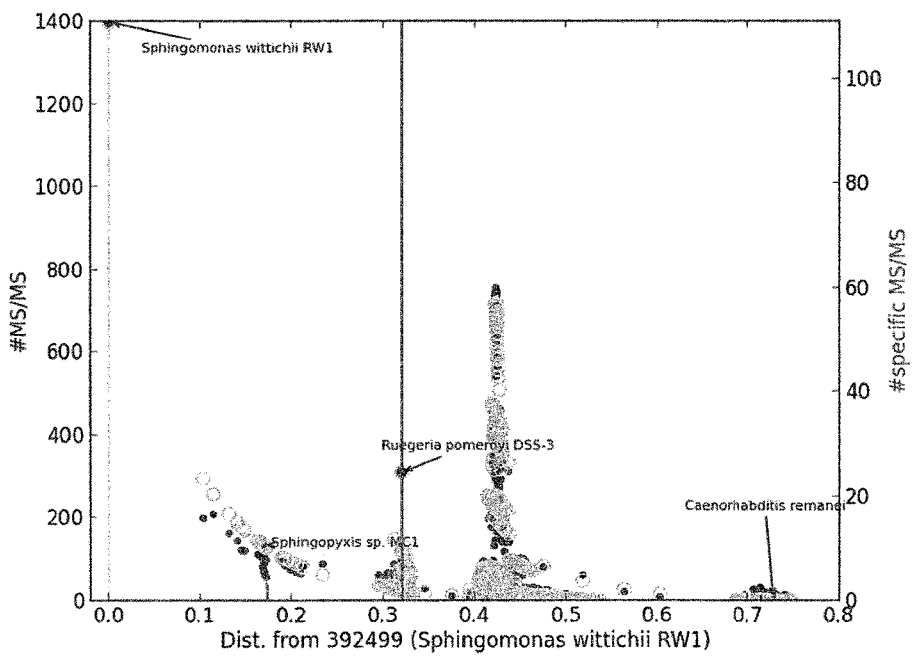

FIG. 17: Final decomposition of the signal for the sample *Sphingomonas wittichii/Escherichia coli/Ruegeria pomeroyi* mixture with our method at the most resolved taxonomical level, and resulting fitting parameters.

$$x<d: y=N^*(A^*\exp(-d/a)+(1-A)^*\exp(-d/b))$$

$$x>=d: y=N^*(A^*\exp(-x/a)+(1-A)^*\exp(-x/b))$$

■Taxon *Sphingomonas wittichii* RW1 (392499)
A=0.60 a=0.0008 b=0.0800 N=2610 d=0.0012
■Taxon *Escherichia coli* BL21 (DE3) (469008)
A=0.60 a=0.0008 b=0.0800 N=1305 d=0.0011
■Taxon *Ruegeria pomeroyi* DSS-3 (246200)
A=0.60 a=0.0008 b=0.0800 N=780 d=0.0064
Fit result: R^2=0.9957

Figure 18:
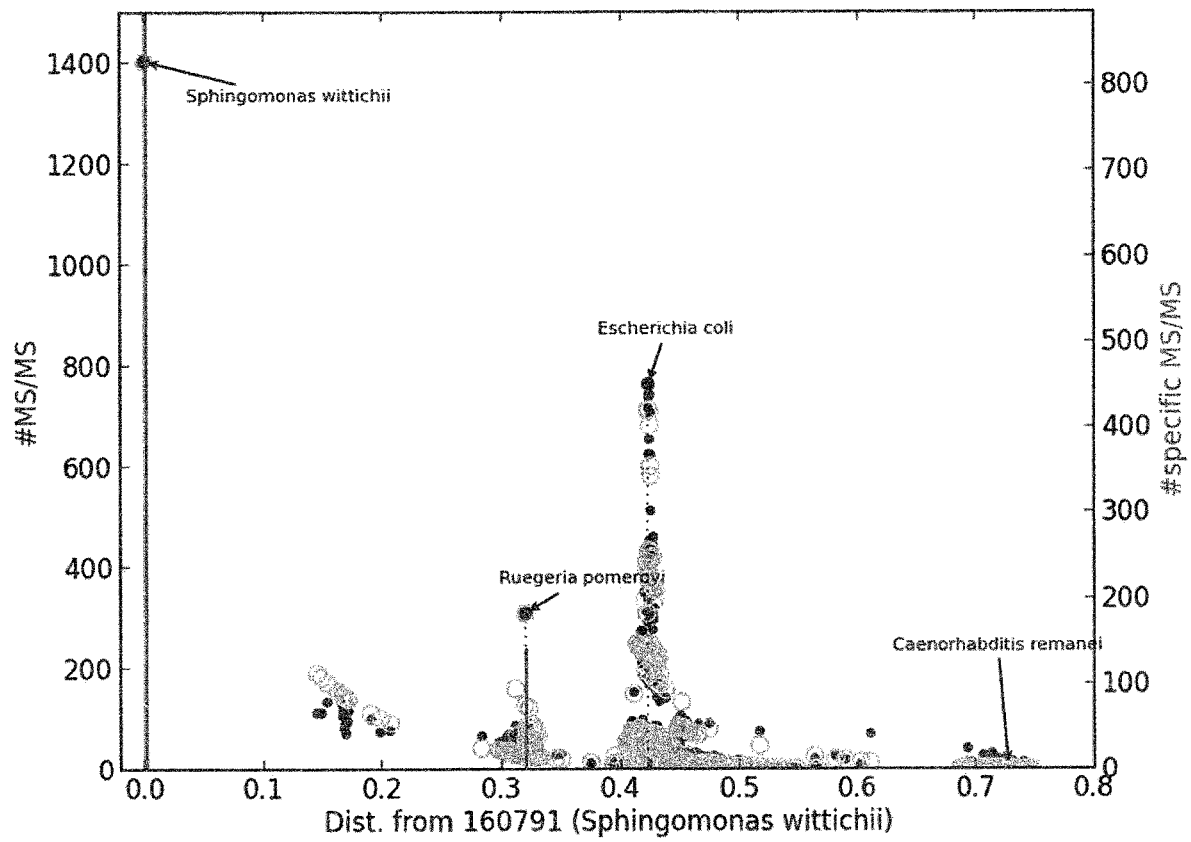

FIG. 18: Final decomposition of the signal for the sample *Sphingomonas wittichii/Escherichia coli/Ruegeria pomeroyi* mixture with our method at the species taxonomical level, and resulting fitting parameters.

$$x<d: y=N^*(A^*\exp(-d/a)+(1-A)^*\exp(-d/b))$$

$$x>=d: y=N^*(A^*\exp(-x/a)+(1-A)^*\exp(-x/b))$$

■Taxon *Sphingomonas wittichii* (160791)
A=0.60 a=0.0010 b=0.0800 N=2808 d=0.0017
■Taxon *Escherichia coli* (562)
A=0.60 a=0.0010 b=0.0800 N=1277 d=0.0013
■Taxon *Ruegeria pomeroyi* (89184)
A=0.60 a=0.0010 b=0.0800 N=844 d=0.0130
Fit result: R^2=0.9757

Figure 19:
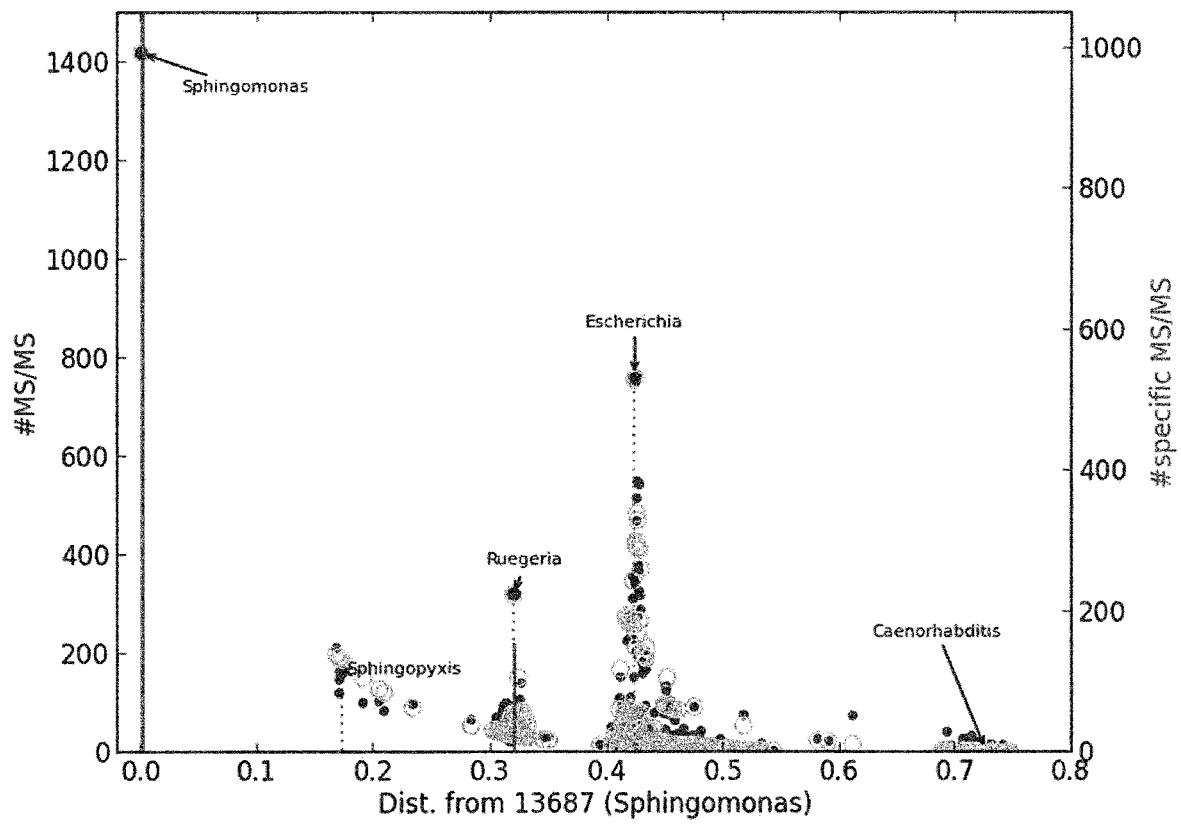

FIG. 19: Final decomposition of the signal for the sample *Sphingomonas wittichii/Escherichia coli/Ruegeria pomeroyi* mixture with our method at the genus taxonomical level, and resulting fitting parameters.

$$x<d: y=N^*(A^*\exp(-d/a)+(1-A)^*\exp(-d/b))$$

$$x>=d: y=N^*(A^*\exp(-x/a)+(1-A)^*\exp(-x/b))$$

■Taxon *Sphingomonas* (13687)
A=0.60 a=0.0008 b=0.0800 N=3906 d=0.0082
■Taxon *Escherichia* (561)
A=0.60 a=0.0008 b=0.0800 N=1435 d=0.0012
■Taxon *Ruegeria* (97050)
A=0.60 a=0.0008 b=0.0800 N=675 d=0.0022
Fit result: R^2=0.9636

1. MATERIALS AND METHODS 1.1 Preparation of Samples

The biological sample is prepared for analysis of its whole protein content by tandem mass spectrometry, for example following the protocol described in (FR1354692) or using standard approach such as described in Mass Spectrometry: A Textbook (Springer, 2011).

In a preferred protocol, the sample undergoes protein precipitation by trichloroacetic acid (10% final), centrifugation in an EPPENDORF centrifuge, removal of the supernatant, pellet dissolved into Laemmli buffer, SDS-PAGE electrophoresis but with a short migration time, excision of a polyacrylamide band containing the whole proteome, reduction and alkylation of cysteines by iodoacetamide, and enzymatic proteolysis by trypsin. The resulting peptides are then washed, concentrated and loaded onto a reverse-phase chromatography column coupled to a mass spectrometer for tandem mass spectrometry analysis.

The sample processed in the experiment reported in FIGS. 3 and 4 was prepared from an *Escherichia coli* BL21(DE3) culture grown in liquid LB medium (Lysogeny Broth, i.e. 10 g tryptone+5 g yeast extract+10 g NaCl for 1 liter of distilled or deionized water). The sample consisted in the equivalent of 250 µl of culture harvested at an optical density (OD) value of 1 as measured at 600 nm (about 1E9 cells). The whole protein content of these cells was subjected to SDS-PAGE and processed with trypsin in presence of ProteaseMax reagent, yielding a solution of 50 µL of tryptic peptides. A fraction (1 µL out of 50 µL) of the resulting processed sample was injected in the mass spectrometer.

The sample processed in the experiment reported in FIGS. 5 and 6 was prepared by mixing two distinct cultures grown separately: *Escherichia coli* BL21(DE3) culture grown in liquid LB medium and *Ruegeria pomeroyi* DSS-3 grown in liquid marine broth. The mixed sample consisted in the equivalent of a volume of 50 µL of *Escherichia coli* BL21 (DE3) culture at DO (600 nm) equal to 5 (about 2E8 cells), added to a volume of 250 µL of *Ruegeria pomeroyi* DSS-3 culture at DO (600 nm) equal to 5 (about 1E9 cells). A fraction (1 µL out of 50 µL) of the resulting processed sample was injected in the mass spectrometer.

The sample processed in the experiment reported in FIGS. 10 to 12 was prepared by mixing two distinct cultures grown separately: *Escherichia coli* and *Yersinia pestis* culture grown in liquid LB medium. The mixed sample consisted in the equivalent of a volume of 50 µL of *Escherichia coli* culture at DO (600 nm) equal to 5 (about 2E8 cells), added to a volume of 50 µL of *Yersinia pestis* culture at DO (600 nm) equal to 5 (about 2E8 cells). A fraction (1 µL out of 50 µL) of the resulting processed sample was injected in the mass spectrometer.

The sample processed in the experiment reported in FIGS. 13 to 19 was prepared by mixing three distinct cultures grown separately: *Escherichia coli* BL21(DE3) and *Sphingomonas wittichii* RW1 grown in liquid LB medium and *Ruegeria pomeroyi* DSS-3 grown in liquid marine broth. The mixed sample consisted in the equivalent of a volume of 50 µL of *Escherichia coli* BL21(DE3) culture at DO (600 nm) equal to 5 (about 2E8 cells), added to a volume of 79 µL of *Sphingomonas wittichii* RW1 culture at DO (600 nm) equal to 3.2 (about 2E8 cells) and to a volume of 433 µL of *Ruegeria pomeroyi* DSS-3 culture at DO (600 nm) equal to 0.6 (about 2E8 cells). A fraction (1 µL out of 50 µL) of the resulting processed sample was injected in the mass spectrometer.

1.2. NanoLC-MS/MS.

Settings and conditions for analyzing the peptides by tandem mass spectrometry are described for the LTQ ORBITRAP XL (ThermoFisher) mass spectrometer, coupled to an UltiMate 3000 LC system (Dionex) equipped with a reverse-phase ACCLAIM PEPMAP100 C18µ-precolumn (5 µm, 100 Å, 300 µm i.d.×5 mm, Dionex-ThermoFisher) followed by a nanoscale ACCLAIM PEPMAP100 C18 capillary column (3 µm, 100 Å, 75 µm i.d.×15 cm, Dionex).

Step 1 Load 1 to 10 µL (maximum volume allowed by the system) of the acidified peptide mixture and resolve over a 90 min linear gradient from 5 to 50% solvent B (0.1% formic acid, 80% acetonitrile in water) using a flow rate of 0.3 µL/min. The loading volume is adjusted as a function of the total current measured by the mass spectrometer to avoid saturating the detector.

Step 2 Collect full-scan mass spectra over the 300 to 1,800 m/z range and MS/MS on the three most abundant precursor ions (minimum signal required set at 10,000, possible charge states: 2+), with dynamic exclusion of previously-selected ions (exclusion duration of 10 sec, one replicate).

1.3. Ms/Ms Assignments.

The resulting RAW file recorded by the mass spectrometer contains MS spectra and MS/MS spectra for MS isotopic patterns corresponding to certain requirements (intensity above 10000, +2 charge). These requirements are associated with peptides that have a high probability of being identified from the corresponding MS/MS fragmentation spectrum. The RAW file is converted to MGF (Mascot Generic File) format using the extract_msn.exe program (ThermoScientific), with options set as follows: 400 (minimum mass), 5,000 (maximum mass), 0 (grouping tolerance), 0 (intermediate scans), 10 (minimum peaks), 2 (extract MSn), and 1,000 (threshold). These options can be set in the Mascot Daemon software (version 2.3.02, Matrix Science) in the options of the Data import filter (ThermoFinnigan LCQ/DECA RAW file). The MGF file is then processed by the Mascot Server (version 2.3.02, Matrix Science, running on a 64-bits computer with an INTEL XEON CPU W3520 @2.67 GHz, RAM 24 GB), using search parameters set in the Mascot Daemon client. The database used is based on the most-updated NCBInr database to allow protein accession-to-organism Taxonomy ID (taxid) mapping. It can comprise the complete database or a non-redundant subset. Other parameters for MS/MS to peptide assignment are: maximum number of missed cleavages set at 2, 5 ppm for mass tolerance on the parent ion, 0.5 Da for mass tolerance on the product ions, carbamidomethylated cysteine residues as fixed modification, and oxidized methionine residues as variable modification. Decoy database search can be selected if a false discovery rate (FDR) needs to be calculated. The Mascot inference process results in a DAT file that can be used as an input for the organism identification program that the inventors have developed and named ptorg.ID.

1.4. Determination of the Number of PSMs Per Taxon with µOrg.ID.

Databases: The NCBI nr database is downloaded weekly on the Mascot server from ftp://ftp.ncbi.nih.gov/BLAST/db/ in fasta format. This database is used both by Mascot for identifications and to create a BLAST formatted database for BLAST searches. The NCBI taxonomy database is also loaded weekly on the server from ftp://ftp.ncbi.nih.gov/pub/taxonomy/. Files used are gi_taxid_prot.dmp for gi to taxid mapping; nodes.dmp for taxonomy level and hierarchy; and names.dmp for taxa names.

Python packages: The Mascot DAT files can be read using the msparser tool (Matrix Science). The Python version of msparser is used (v2.4.02) and interfaced with a complete package written in Python (v2.6.6).

Additional packages to the Python installation include biopython (v1.55), lxml (v3.0.1), numpy (v1.6.2), scipy (v0.9.0), poster (v0.8.1), pysqlite2, tablib (v0.9.1), and ujson (v1.23). A Python library from ThermoScientific, msfilereader, can also be used to access RAW files (in which case python package comtypes (v0.6.2) is needed).

1.5. Determination of the Distances Between Taxa with µorg.ID:

Software tools: clustalw.exe (v2.1), muscle.exe (v3.8.31), and BLAST (v2.2.27+) are installed on the Mascot server. The NCBInr fasta files are processed to create a BLAST database using the makeBLASTdb.exe utility with the options parse_seqids and hash_index set and the following parameters: prot (dbtype), gi_taxid_prot.dmp (taxid_map), NCBInr (title), and NCBInr (out).

Python packages: In addition to the previous packages, dendropy (v3.12.0) is installed for this task.

Supervector for phylogenetic distance estimation. The method chosen for distance estimation is based on Ciccarelli et al., which has been corrected by correction of taxa in accordance with current NCBI taxonomy to allow the calculation of phylogenetic distances based on protein information between any taxa from the NCBI database.

1.6. Signal Deconvolution With µorg.ID:

Software tools: Curve fitting and signal deconvolution are performed in Excel (Microsoft Office 2010), using VBA macros and the solver for curve fitting (GRG non linear, default options). Alternatively, they can be performed with any tools efficient for mixture model analysis, including the evaluation of the number of components, for example using scipy functions, such as curvefit and the Levenberg-Marquardt algorithm, using the Jacobian matrix of the correlation function for curve fitting.

1.7. EXtracted Ion Chromatograms

An in-house software written in Python was used to gather MS intensity information associated to each MS/MS spectrum. Python packages include msparser (Matrix Science) used to access Mascot DAT files and msfilereader (ThermoScientific) used to access RAW files. The ranges to collect intensity data associated to a PSM were 1.2 ppm for the m/z window compared to the peptide m/z, and 300 s compared to the retention time (RT) of the MS/MS considered. All MS scans, acquired at 1 Hertz, where processed with these m/z and RT ranges to extract the full XIC, and collect the maximum intensity value associated with each PSM.

1.8. DNA Data Analysis

Unassembled whole genome sequencing (WGS) data were downloaded for a typical *Escherichia coli* sequencing on an Illumina HISEQ 2000 sequencing system for ERR163875. A first random SRA subset (14,448 reads) was transformed to fasta format using the SRA toolkit (NCBI) to convert SRA to fastq, then the BioPython SeqIO.convert function was used to obtain a fasta file. This file was used as a query for a BLASTn search on NCBI nt with default parameters except for a E-value at 1e-20. A second subset of 14,428 reads was then selected on the double criteria: (i) 200 bp sequence with no undetermined nucleotide (N) and, (ii) at least one BLAST hit with a E-value below 1e-20. A Python script was written to associate organism information to each read using the "Hit_def" field from the XML BLAST output after minor "Hit_def" curation to homogenize species naming. The final output in Table VI also includes a numbering of reads only associated with the species taxa listed.

2. RESULTS 2.1 Definition of "Peptide Spectrum Matches" and Database Comparison.

The first step of the procedure consists of the assignation of peptide sequences to the MS/MS spectra recorded by tandem mass spectrometry. For this, the inventors used the MASCOT software with standard parameters. The efficiency of MS/MS spectra assignment using the current peptide extraction protocol for samples corresponding to either Gram+ or Gram− bacteria is indicated in Table I by the assignment ratio. This ratio is the number of spectra assigned by Mascot to a peptide sequence from the database at a confidence value p below 0.05, also called Peptide Spectrum Matches (PSMs). On a small database extracted from NCBInr corresponding to the annotated proteome of a known organism, the ratio of assigned MS/MS spectra per recorded spectra in our experimental set-up varies from 63 to 71% at a confidence value of 95% (p<0.05) for data recorded for this specific organism. On the complete NCBInr database (release of Apr. 19, 2013), which contains over 5,000 times more amino acids, the ratio drops to 27 to 35% even at a confidence value of 90% (p<0.10) because of a higher number of peptides matching the m/z value of the parent solely by chance. For example, an average of 4,405 PSMs were obtained for *Escherichia coli* BL21(DE3) sample against the *Escherichia coli* BL21(DE3) database while only 1981 PSMs were obtained on the NCBInr database at the same p value threshold 0.05 (Table I). However, these values are indicative of the number of PSMs expected in the current process. Unless otherwise specified, data shown in this document have been collected on the complete NCBInr database and at a p-value below 0.10. (Note: alternatively, or as a post-treatment, a faster Mascot search will be obtained by selecting a subset of the NCBInr based on a unique taxon per genus, selected for being representative of the number of proteins in the genus and for good sequencing quality (complete status on NCBI genomes—www.ncbi.nlm.nih.gov/genome or GOLD—www.genomesonline.org). This reduced database allows a higher number of PSMs than with the whole NCBInr database in a first faster coarse-grained Mascot search, while retaining the capability to identify the different genera represented in the sample. In this scheme, once a genus is found in the sample in the first search, all leaf taxa from the corresponding family are gathered to build a second database including all possible strains or species in the sample. The analysis of this second Mascot search can be used for a fine-grain identification of the organisms in the sample).

TABLE I

Efficiency of MS/MS spectra assignments for pure organisms using a dedicated protein database extracted from the NCBInr or the complete protein NCBInr database.

| | | Dedicated DB | | NCBInr DB | | | |
|---|---|---|---|---|---|---|---|
| | # MS/MS | # PSMs (p < 0.05) | % Assignments (p < 0.05) | # PSMs (p < 0.05) | % Assignments (p < 0.05) | # PSMs (p < 0.1) | % Assignments (p < 0.1) |
| *Escherichia coli* BL21(DE3) | 6722 | 4542 | 68% | 2090 | 31% | 2308 | 34% |
| GRAM− | 6437 | 4381 | 68% | 1946 | 30% | 2146 | 33% |
| | 6054 | 4292 | 71% | 1906 | 31% | 2101 | 35% |
| Average | 6404 | 4405 | 69% | 1981 | 31% | 2185 | 34% |
| Standard deviation | ±335 | ±127 | ±2% | ±97 | ±1% | ±109 | ±1% |
| *Bacillus cereus* ATCC 14579 | 5297 | 3575 | 67% | 1374 | 26% | 1562 | 29% |
| GRAM+ | 5325 | 3373 | 63% | 1309 | 25% | 1454 | 27% |
| Average | 5311 | 3474 | 65% | 1342 | 25% | 1508 | 28% |
| Standard deviation | ±20 | ±143 | ±3% | ±46 | ±1% | ±76 | ±2% |

2.2. Determination of Number of PSMs Per Taxon With µorg.ID.

The next stage of the process is to attribute spectra to taxa, using PSMs from the Mascot search. Classical proteomics tries to maximize the protein inference confidence by means such as parsimony (a rule which attributes each spectrum only to the most probable protein, i.e., with the highest number of spectra or peptides attributed) or a minimum of 2 different peptides to validate a protein (see the journal "Molecular and Cellular Proteomics" current guidelines available at www.mcponline.org/site/misc/PhialdelphiaGuidelinesFINALDRAFT.pdf).

The µorg.ID procedure does not involve the interpretation of data in terms of proteins, instead all the information available is used to estimate a quantitative representative of the contribution of an organism in a complex sample, possibly in a mixture. Conservation of tryptic peptide sequences is such that many sequences can be found in several organisms from different clades because they are in conserved regions of widespread conserved proteins. The co-occurrence of such conserved peptides is higher for closely-related organisms than far-related organisms. Table II shows this level of conservation for a specific dataset (*E. coli* BL21(DE3)) at the phylum level. A total of 14% of peptides found associated with the proteobacteria phylum are also found associated to the next phylum, streptophyta (266 amongst 1915), or more than 10% in another phylum, firmicutes. To be able to identify, but also and most importantly quantify, different organisms in a mixture, it is thus mandatory to exclude parsimony methods that will favor the most prominent organism detrimentally to the others, and to attribute each MS/MS spectrum to all possible corresponding taxa taking care of the contributions of conserved patterns in a post-treatment.

TABLE II

Peptide conservation between phyla for an *E. coli* BL21(DE3) pure sample, i.e., pure proteobacteria phylum (human contamination (due to keratins) very low, as shown by a low number of specific PSMs in the chordata phylum (48), validated by 3 specific PSMs).

| Name | Taxid | Tax Rank | Super-kingdom | # PSMs | # Specific PSMs | # Peptides |
|---|---|---|---|---|---|---|
| Proteobacteria | 1224 | phylum | Bacteria | 2329 | 1370 | 1909 |
| Streptophyta | 35493 | phylum | Eukaryota | 439 | 0 | 266 |
| Firmicutes | 1239 | phylum | Bacteria | 301 | 0 | 201 |
| Arthropoda | 6656 | phylum | Eukaryota | 271 | 0 | 146 |
| Actinobacteria | 201174 | phylum | Bacteria | 118 | 1 | 75 |
| Bacteroidetes | 976 | phylum | Bacteria | 96 | 0 | 61 |
| Chordata | 7711 | phylum | Eukaryota | 48 | 3 | 26 |

To enable fast association of PSMs to taxonomical information, a sqlite database is built using Python with 3 tables. The first table is called 'gi2firstgi' and associates each gi from the NCBInr with the first gi listed in the fasta file if they correspond to the same polypeptide sequence. Note that a gi is a unique identifier of a given polypeptide in the NCBI database. All gis associated with the same "first" gi thus share exactly the same polypeptide sequence, summarizing the non-redundancy information in the NCBInr database. This table is created from a parsing of all headers from the NCBInr database. The second table called 'gi2taxid' is created directly from the gi_taxid_prot.dmp NCBI taxonomy file and associates gis (master key) to taxids. The third table called 'taxid2nbgis_nbseqs' associates taxids (i) with the number of gis per taxid by querying each taxid in the second table (gi2taxid) and (ii) with the number of different sequences, using the first table (gi2firstgi) to identify redundant gis of identical sequence (one gi for the NCBI RefSeq and one for the Genbank accession, for example).

To associate PSMs to taxa (see FIG. 1), a first listing of all PSMs above the p-value threshold is compiled from the DAT file using msparser, allowing the mapping of spectra to peptides. This stage is not limited to the PSM of highest score for each spectrum because the inventors address sample mixtures without parsimony requirements. All proteins containing each peptide are then associated to each spectrum using the msparser, and Table gi2firstgi is used to enlarge protein mapping to all proteins, redundant or non-redundant. Table gi2taxid is then used to convert gis to taxids and obtain an association of each spectrum with a list of unique taxids.

Proteins corresponding to the Protein DataBank are excluded because many structures are obtained with mutated sequences, resulting in abnormal taxon specific spectra.

File nodes.dmp (taxonomic hierarchy and level information) is processed, and the spectrum-taxa information is reversed to obtain a list of spectra per taxon, including sub-taxon aggregation for Glade taxa. Spectra lists for each taxon are finally uniquified before counting spectra per taxon. In the case of bacteria, where the "no rank" level can correspond to strains, the aggregation of several sub-taxa of the same "no rank" level was performed, but sub-taxa were also listed in the same evaluation. This result corresponds to a table including both "no rank" and leaf taxa, which also allows the evaluation at the finest taxonomical level of bacterial leaf taxa only referenced at the species level.

In addition to the number of PSMs per taxon, a counting of unique (or specific) PSMs is performed for each taxon, indicating the number of PSMs that are only associated to each given taxon. Table II lists a subset of such information at the phylum level and Table III at the "no rank+leaf" level, i.e., the most resolute level, for the same pure *E. coli* BL21(DE3) strain sample. Species *Escherichia* sp. 1_1_43 appears in Table III because it has no "no rank" sub-taxon. Taxon 37762 for *E. coli* B collects 2288 PSMs for only 97 sequences in the database because of its sub-taxon (taxid 413997).

The post-process of a DAT file is very fast, and tabulated text files giving PSM counts per taxon at the "superkingdom", "phylum", "class", "order", "family", "genus", and "no rank" leaf taxonomic levels are generated in a few minutes. For example, in the search used for Tables II and III, 2,346 MS/MS spectra are assigned to at least one peptide, corresponding to a total of 103,872 different protein sequences in the NCBInr database (v2013/04/23), 1,386,243 different gi accessions associated with these sequences, and finally 19,904 different taxids. The complete process took about 7 minutes.

TABLE III

Numbering of PSMs per taxon at the most resolute level, i.e. the "no rank + leaf"
level, and at the species level for selected taxa, for a an *E. coli* BL21(DE3) pure sample.

| Name | Taxid | Tax Rank | Super-kingdom | # sequences | # MS/MS | # specific MS/MS | # peptides |
|---|---|---|---|---|---|---|---|
| *Escherichia coli* BL21(DE3) | 469008 | no rank | Bacteria | 4380 | 2315 | 0 | 1321 |
| *Escherichia coli* 'BL21-Gold(DE3)pLysS AG' | 866768 | no rank | Bacteria | 4156 | 2315 | 0 | 1321 |
| *Escherichia coli* H489 | 656404 | no rank | Bacteria | 4525 | 2301 | 0 | 1311 |
| *Escherichia coli* B | 37762 | no rank | Bacteria | 97 | 2286 | 0 | 1306 |
| *Escherichia coli* B str. REL606 | 413997 | no rank | Bacteria | 4144 | 2286 | 0 | 1306 |
| *Escherichia* sp. 1_1_43 | 457400 | species | Bacteria | 4478 | 2284 | 0 | 1298 |
| *Escherichia coli* KTE197 | 1181743 | no rank | Bacteria | 4336 | 2279 | 0 | 1295 |
| *Escherichia coli* KTE51 | 1182658 | no rank | Bacteria | 4908 | 2279 | 0 | 1295 |
| *Escherichia coli* str. K-12 substr. W3110 | 316407 | no rank | Bacteria | 4355 | 2277 | 0 | 1297 |
| *Escherichia coli* | 562 | species | Bacteria | 695176 | 2325 | 15 | 1356 |
| *Escherichia* sp. 1_1_43 | 457400 | species | Bacteria | 4636 | 2284 | 0 | 1298 |
| *Bos taurus* | 9913 | species | Eukaryota | 44032 | 5 | 2 | 2 |
| *Photorhabdus asymbiotica* | 291112 | species | Bacteria | 4385 | 487 | 1 | 274 |

2.3 Distances Between Taxa Evaluated With µorg.ID.

The original method reported by Ciccarelli et al. to reconstruct a highly resolved tree of life relied on the selection of 31 Clusters of Orthologous Groups (COGs), which were conserved in all superkingdoms, and thus allowed the calculation of distance matrices between all known fully sequenced organisms at that time (year 2006). It was based on 191 taxa (23 archaea, 18 eukaryota, 150 bacteria), and resulted in a multiple sequence alignment (MSA) of supervectors obtained through a concatenation of the 31 COGs for a complete MSA of 8090 amino acid positions.

This method was chosen for the phylopeptidomic approach as a starting point for the automation of the calculation of a phylogenetic distance between taxa for several reasons. First, the data used are similar to the data collected in tandem mass spectrometry experiments, i.e., partial protein sequences. With current instruments and complex samples, concentration ratios for visible peptides are limited by the dynamic range of the instruments, currently at about 4 orders of magnitudes. With protein concentration ratios ranging from 7 for bacteria to 10 orders of magnitudes for eukaryotes, only the MS/MS detectable peptides from the most abundant proteins are consistently analyzed, corresponding in general to more conserved proteins of the key cellular functions (such as proteins involved in translation) rather than proteins of higher specificity. A second reason is the availability of fast tools such as BLAST to identify COGs homologues in any given proteome. A third reason is the stringency of the method, where pre-existing alignment of COGs can serve as a frame, following some curations. A first synchronization of COGs sequences used in the alignment with current sequences and sequences-to-taxon associations has been performed, to match data reported in the NCBI taxonomy history files. In addition to this curation, 11 taxa have been removed from the reference alignment to suppress sequence redundancy.

The methodology to add a new taxon to the root MSA is to identify the closest taxon ("reference taxon") in the root MSA using NCBI taxonomy hierarchy information. COGs sequences for the reference taxon (COGs_fasta) are then queried using BLAST against the NCBInr filtered with the list of gis corresponding to the taxid to be added. This list of gis (gi_list) is easily extracted from the gi2taxid sqlite table for the new taxid. The BLASTp.exe utility is run with optimized parameters: COGs_fasta (query), gi_list (gilist), 1 (max_target_seqs), 9 (gapopen), 1 (gapextend), BLOSUM90 (matrix). Once identified, the gi representative of each COG in the new taxon is aligned against the reference COG using the MUSCLE software program. This alignment is characterized by a % coverage and a % identity index, and replaced by gaps if the result is obviously a bad match. For these conserved proteins, an identity percentage below 60% is used as a threshold to identify an adequately sequenced COG representative. Finally, residues and gaps for the reference COG are used as a template to define the portions of the new sequence to be added to the MSA. The supervector of the new taxon can thus be defined and added to the MSA.

When all taxa are added, CLUSTALW is used to generate a phylip tree (.ph), using the neighbour-joining algorithm to construct the tree. Finally, a patristic distance matrix is extracted from the phylip tree, using for example the R program or the dendropy package in Python. Although clustalw is not a phylogeny tool, the distance error compared to PHYML or Phylip's PROTDIST are minor compared to the time taken for bootstrapping in more evolved methods.

2.4 Deconvolution of the PSMs Signals With µorg.ID.

Correlation Function

A plot of the number of PSMs assigned to each taxon against the phylogenetic distance between the taxon of highest number of PSMs and all others, using the methodology detailed above, demonstrates an excellent correlation between both variables, whatever the taxonomical rank considered. FIGS. 3 and 4 were plotted at the strain and genus taxonomic level, respectively. The lower graphs showing residual signal on each figure are obtained by subtracting to the number of PSMs per taxon a correlation function in the following form:

$$Y = N \times (A \times e^{(-X/d1)} + (1-A) \times e^{(-X/d2)}).$$ Formula 0

In this formula, N is the number of PSMs attributed to the taxon chosen as the reference for distances calculation (X-axis), A is the percentage of the exponential term in the form $e^{-X/d1}$, with the complement to 1 attributed to the second exponential term in the form $e^{-X/d2}$. The parameters of this function are fitted to minimize a convergence criterion, representative of the differences between data points and function.

An improved model includes a function by parts, adapted to non-sequenced organisms. An additional parameter d is used, indicative of the phylogenetic distance between the best taxon found in databases, and the actual organism in the sample. The revised function is in the form:

$$0 \leq X < d: Y = N \times (A \times e^{(-d/d1)} + (1-A) \times e^{(-d/d2)}).$$

$$d \leq X: Y = N \times (A \times e^{(-X/d1)} + (1-A) \times e^{(-X/d2)}). \quad \text{Formulae 1}$$

In FIGS. 3 and 4, the latter function was used, with parameters d1 and d2 fixed to 0.0122 and 0.0733 respectively, and parameters N, A and d fitted, using a non-linear adjustment method. FIGS. 3 and 4 were fitted using the "GRG nonlinear" method of Excel 2010 solver, adjusting the sum of absolute differences between data points and function to 0. Alternatively, nonlinear methods such as Levenberg-Marquardt could be used, using the Jacobian matrix holding partial derivatives of the function described (or a sum of such functions in the case of a mixture of organisms) with respect to each of the parameters, or whatever adapted method known from the art.

Two important observations are drawn from the evaluation of the remaining signal after subtraction of a fitted function to the data points. In FIGS. 3 and 4 corresponding to a pure organism sample, the (#PSMs-FIT) residual signal does not display a consistent pattern of taxa with positive residual signal. In contrast, FIGS. 5 and 6 with known mixtures of organisms display a residual signal with very strong pattern of taxa in the same phylogenetic distance range. Assessing the presence of additional organisms in the sample should thus preferably be based on a discrimination criterion based on taxa clustering or methods to evaluate the number of components in a mixture model rather than individual taxon evaluation.

2.5 Mixture of Organisms

Data shown in FIG. 5 and FIG. 6 correspond to the number of PSMs per taxon for a sample prepared by mixing a fraction of two cultures of microorganisms, namely *Escherichia coli* BL21 (DE3) (taxid: 469008) and *Ruegeria pomeryoi* DSS-3 (taxid: 246200), as detailed in Materials and Methods. The amounts used, equivalent to 250 µl at an OD of 1 for *R. pomeroyi* and ⅕ of this amount for *E. coli*, should correspond to a ratio of cells for *R. pomeroyi:E. coli* equal to 5.

For n taxa of indice k, the fit formula is:

$$Y = \sum_{k=1}^{n} Y_k \quad \text{Formula 2}$$
$$= \sum_{k=1}^{n} N_k \left[ A_k \left( e^{-X_k/d_{1,k}} \right) + (1 - A_k) \left( e^{-X_k/d_{2,k}} \right) \right]$$

where:
$N_k$=number of deconvoluted PSMs corresponding to taxon k
$X_k$=phylogenetic distance of each taxon relatively to taxon k
$A_k$=fraction of the first exponential term for taxon k
$d_{1,k}$=parameter for the first exponential term for taxon k
$d_{2,k}$=parameter for the second exponential term for taxon k The fit in FIG. 6 was performed with a mixture of two functions of the type Function 1:

$$Yc + Yr = Nc(Ac^* e^{(-Xc/d1c)} + (1-Ac)^* e^{(-Xc/d2c)}) + Nr(Ar^* e^{(-Xr/d1r)} + (1-Ar)^* e^{(-Xr/d2r)})$$

where:
Nc=number of deconvoluted PSMs corresponding to *E. coli*
Xc=phylogenetic distance of each taxon relatively to taxid: 469008
Ac=fraction of the first exponential term for *E. coli*
d1c=parameter for the first exponential term for *E. coli*
d2c=parameter for the second exponential term for *E. coli*
Nr=number of deconvoluted PSMs corresponding to *R. pomeroyi*
Xr=phylogenetic distance of each taxon relatively to taxid: 246200
Ar=fraction of the first exponential term for *R. pomeroyi*
d1r=parameter for the first exponential term for *R. pomeroyi*
d2r=parameter for the second exponential term for *R. pomeroyi*

Fitted values were, using Excel solver to minimize the objective function f=Y−Yc−Yr:
Nr=1822, Nc=568, Ar=0.3091, d1r=0.0122, d2r=0.0885, Ac=0.527, d1c=0.0122, d2c=0.075.

Deconvoluted number of PSMs, Nr and Nc, represent the number of spectra attributed to each organism, excluding the fraction of PSM resulting from the presence of other organisms in the mixture.

The deconvolution process to identify taxa in a mixture sample can either be iterative or concurrent. At a given taxonomical level, the current data indicates that a generic value for parameter d1 can be found, and d2 and A might need to be slightly adjusted per Glade (for a given PSM confidence level). They have yet to be adapted to different values for different taxonomical levels.

Function 2, by parts, can be used to deconvolute the signal of a non-sequenced organism.

Data processing for FIGS. 12,16,17,18 and 19 was performed using signature functions based on function 2 only, and a minimization of the objective function defined as the sum of squared errors by fitting of parameters A, N and d (from function 2) for each identified taxon k. Fixed parameter values are in the figure legends. The Python package: scipy.optimize method leastsq was used for non linear parameter fitting.

The global process can be itemized in 8 stages following the prior sample preparation and processing on a LC-MS/MS instrument:

1. Association of spectrum to peptides using an external inference tool (such as the Mascot software program), and a standard or dedicated database (NCBInr or subset in the embodiment).

2. Association of peptides to taxa at the leaf level using a taxonomy database (NCBInr or subset in the embodiment).

3. Selection of a taxonomy level (genus in first loop depending on the complexity of the sample and the taxonomy level searched) and counting of spectra per taxon.

4. Selection of the most probable organism (taxon), and use of the (Total number of spectra per taxon)/(phylogenetic distance) correlation function to deconvolute the corresponding signal. The fitted parameters include the number of spectra per taxon.

5. Analysis of residual signal to identify remaining organisms in the sample, and loop to stage 4 until the residual signal is at the noise level.

6. Global fit with a taxon selection latitude.

7. Loop to stage 1 once, with a specific subset of the database (e.g. families containing identified genus) 8. Loop to stage 3 until lowest taxonomical level is reached depending on the objectives of the search (species for eucaryota, strain for bacteria for example).

The deconvoluted amount of PSM is very similar to the number of spectral counts (SC) used in comparative proteomics to quantify ratios of proteins in different conditions.

Mixtures of *Escherichia coli* BL21(DE3) and *Ruegeria pomeroyi* DSS-3 at three different ratios were used to exemplify relative quantification of mixtures. Table IV shows that ratios based on the deconvoluted number of spectra per taxon are correlated with ratios estimated by optical density measured at 600 nm prior mixing the organisms (an estimation of the number of cells or the protein-equivalent content for each strain could also be performed by other means, for example by Malassez cell counts, cell mass (wet or dry), or bradford quantitation of protein whole cellular extract). A more accurate relative quantification between the organisms can be performed by replacing each PSM by the intensity of the parent ion as detailed in Material and Methods. The XIC based quantification of a taxon can then be computed for example using the sum of a subset comprising the 100 most intense XICs associated to it, as shown in FIG. 7. The correlation of this quantitation with distances between taxa was also used to deconvolute in particular the contribution of PSMs shared between organisms, which is a crucial problem for closely related organisms. The function fit in FIG. 7 was obtained using the same function as previously described and the following parameters: Nr=3.65E9, Nc=4.67E9, Ar=Ac=0.7, d1r=d1c=0.002, d2r=d2c=0.13 (r indice=*R. pomeroyi*, c=*E. coli*). A better estimation of the ratio of any sample can be obtained after normalizing the intensities with a measurement where the ratio is known such as the 1:1 ratio as done in Table IV.

Any other mass spectrometry-based quantitative methods could also be applied to associate an intensity value to each PSM signal, such as the Total Ion current (TIC) of the MS/MS spectrum.

Optical Density as measured at 600 nm. Results are shown in Table V. While spectral counts give a M12/M3 ratio of 1.4, the sum of the Top10 XICs gives a ratio of 10.3. Because the reference sample M3 corresponded to 2.5 E8 cells, then the M12 sample was estimated to contain 2.575 E9 cells based on the Top10 XICs method.

TABLE V

Quantification of 2 samples of *E. coli* BL21 of cells contents in a ratio of 1/10, as estimated by OD. Sum of Top10 XIC gives an accurate ratio estimate, thus absolute quantitation if a reference is known.

| Sample n°. | Eq. OD | # PSMs | Sum of Top10 XICs | Number of cells |
|---|---|---|---|---|
| M3 (reference) | 1 | 2255 | 5.90E+08 | 2.5 E8 cells |
| M12 | 10 | 3063 | 6.08E+09 | 2.575 E9 |
| Ratio M12/M3 | 10 |  | 1.4 | 10.3 | 10.3 |

2.6 Non-Sequenced Organisms

Function 2, which is detailed above, can be used to analyze a sample containing organisms with unsequenced genomes or not present in the search database. Such condition was simulated using data from FIGS. 3 and 4. Distances between the strain effectively present in the sample, i.e. *Escherichia coli* BL21(DE3), taxid: 469008, and other taxa have been used to identify the first taxon at a distance above 0.025. In this case, the first organism identified was *Cronobacter sakazakii* ES15 (taxid: 1138308), at a distance of 0.0251. This organism is from the same family as *Escherichia coli*, namely the Enterobacteriaceae family (Enterobacteriales order). FIG. 8 was plotted using taxid 1138308 as the reference organism for X values, and displaying only taxa at a distance from taxid 469008 above 0.025. The best fit of function 2 to the data was obtained with the following parameters: d=0.0288, N=2327.4, A=0.406, d1=0.0122, d2=0.0733.

TABLE IV

Relative quantification of dilutions of *E. coli* BL21 to a reference organism: *R. pomeroyi* DSS-3, and comparison of OD ratios to the MS quantification methods using deconvoluted #PSMs and XIC values.

| Mix based on OD | *R. pomeroyi* DSS-3 # PSMs | *E. coli* BL21 # PSMs | *R. pomeroyi* DSS-3 Top100 XICs | *E.coli* BL21 Top100 XICs | % *E. coli* BL21/*R. pomeroyi* DSS-3, normalized with the 1:1 measurement | | |
|---|---|---|---|---|---|---|---|
| | | | | | based on OD | based on #PSMs | based on XIC |
| 1:1 | 781 | 1836 | 1.84E+09 | 2.99E+09 | 100% | 100% | 100% |
| 1:0.5 | 1248 | 1237 | 2.21E+09 | 1.76E+09 | 50% | 42% | 49% |
| 1:0.2 | 1822 | 568 | 2.62E+09 | 8.67E+08 | 20% | 13% | 20% |

Absolute quantification of pure samples is also within reach, but requires a calibration curve to correlate the taxon signal to a signal representative of a number of cells in the sample.

This calibration depends on (i) the correspondence between number of cells and peptides amounts for different cell types, (ii) the protocol leading to a digested sample from a cell extract, (iii) the characteristics of the separation process before introduction in the mass spectrometer, (iv) the mass spectrometer capacity to process exhaustively all peptides ions at any elution stage (v) the mass spectrometer reproducibility for varying complex samples. A test was performed with a selected organism (*E. coli* BL21) for which two cell amounts were processed similarly. The two samples, M3 and M12, differed by a ratio of 10 in terms of Interestingly, parameter d (0.0288) is close to the distance used to exclude taxa (0.0250), and is thus an indicator of the distance between the organism in the sample and the closest representative in the database used for fitting. The sensitivity of this indicator of phylogenetic distance has been assessed on the same sample by removing all *Escherichia coli* strains up to a distance of 0.0009 from strain *E. coli* BL21(DE3), corresponding to the first organism of a different species, namely *Shigella flexneri* 2a str. 2457T (taxid: 198215). This organism is from the same family as *Escherichia coli*, namely the Enterobacteriaceae family (Enterobacteriales order), and closely-related to *Escherichia* genus representatives. Setting this organism as the reference organism for distances selection from the distance matrix, the best fit is obtained with a parameter d of 0.0005, whereas d is found at 0 when the reference organism is the correct one for the sample. The method is thus sensitive enough to identify sequenced organisms at the strain level, but also to characterize if the identification of an unsequenced organism is correct even at the species level.

2.7 Confidence Level

The most direct identification data is the number of spectra specific of a given taxon, at each taxonomical level. The dramatic increase of sequenced organisms leads to a lowering of this information to the noise level, in particular at the strain or even the species level. This is already the case for *Escherichia coli* strains, which identification at the strain level can no longer be performed relying only on this information as shown in Table III. The number of deconvoluted spectra per taxon is much more informative, and even essential in case of a mixture of organisms.

Both information can however be confronted to estimate an identification confidence factor.

Data available to evaluate the confidence level of an identification are:

number of MS/MS in an experiment and total ion chromatogram (TIC) profile. This number is useful to characterize the sample in terms of complexity.

number of PSMs at different expectation values for the spectrum to PSM inference (p-value of a match by chance using Mascot, see Table I). The ratio of assigned MS/MS spectra is modulated by sample quality, sample quantity, sample complexity, database suitability, mass spectrometer and reverse phase chromatography parameters and calibration, proteolysis efficiency and sample handling.

number of PSMs per taxon, and number of specific PSMs per taxon for each taxonomical level. At a low resolution taxonomical level, the number of specific PSMs and thus the confidence level is high (Table II). For low specific PSMs numbers, a confidence level can be estimated from the search p-value and the number of specific PSMs.

a search on a reduced database including all probable taxa can be performed to estimate the number of MS/MS spectra that are not associated with database sequences. This occurs either because taxon(s) are missing, or other reasons related to sample complexity such as: MS/MS spectra including a mixture of peptides, accuracy of MS masses degraded because of missing internal calibration.

fit parameters:

d in function 2 is directly indicative of database suitability deconvoluted numbers of PSMs and sum of deconvoluted numbers of PSMs at different taxonomical levels can be confronted fit estimator: the fit quality can be used to assign a probability of correct assignment. For example, in a mixture model, the number of components (number of taxa in a mixture at a given taxonomical model) can be evaluated.

An example is given hereafter with data corresponding to FIGS. 5 and 6, at the species level, with taxa 89184 and 562 (for *Ruegeria pomeroyi* and *Escherichia coli* respectively). The numbers of associated PSMs are: 1823 and 594 respectively, and the numbers of specific PSMs are 893 and 12, at an expectation p-value of 0.1 on the full NCBI nr database. The confidence level for both species is thus very high, since each attribution has a 10% chance to be by chance only, corresponding to a probability of attribution by chance of $0.1^{893}$ and $0.1^{12}$ respectively. The confidence at the strain level can however not be based on specific peptides for *E. coli* strains, since no specific PSMs are found for the *E. coli* BL21(DE3) strain. Using the fit by 2 functions as indicated for FIG. 6, the quadratic sum of errors was 209.5 using *E. coli* BL21 (DE3) strain, and 215.4 using the completely sequenced organism closest to *E. coli* BL21 (DE3), i.e. taxid 1050617, strain *E. coli* UMNF18. The fit quality can thus be used for a confidence status at the strain level, and at the species level where the specific PSMs signal will decrease steadily in the following years due to the large sequencing data currently generated. Quantification of the confidence might require a calibration of the fit information, or the generation of random information to evaluate probabilities (bootstrap analysis).

2.8 DNA or RNA Nucleotide Sequence Data

To apply the proposed method to DNA sequencing data or RNA sequencing data, the inventors chose to process Sequence Read Archive (SRA) data from a randomly selected *Escherichia coli* Whole Genome Shotgun (WGS) project. Data shown was obtained for a subset of ERR163875.sra file, processed as detailed in Material and Methods. The length of reads was 200 base pairs, which is currently the higher range of reads for Next-generation Illumina HISEQ or Ion Torrent sequencing technologies (Shokralla, 2012), and thus the most informative.

After matching components (here DNA reads) to taxa using blast searches, the inventors examined if the component-taxon relation was 1 to n, as indicated in FIG. 2. The answer was obviously yes, since it is well known that even using DNA barcodes of 650 bp length for cytochrome oxydase (COI) or 1500 bp for 16S RNA, the specificity is at the species or even the genus level at best. The numbering of reads per taxon at the species level is shown for the top 10 species in Table VI. The inventors then plotted for the species taxa the number of reads against the distance between each taxa and *Escherichia coli*, calculated using the same COGs-based method as previously. FIG. 7 shows that DNA reads data can be modelled using the same type of function as formula 1 for peptide tandem mass spectrometry data, with different d1 and d2 parameters to account for different component specificity (fitted values were: d1=0.007, d2=0.060, A=0.948). For 100 bp read, the fit function would obviously be intermediate between the two plotted curves.

A correlation function between DNA read counts per taxon and taxa distances can thus be established, and used to deconvolute species in a mixture of organisms, satisfying all requirements set forward in FIG. 2 to identify a field were the invention can be applied. A quantification of organisms could also be processed by using for instance a measure of the redundancy of each read, in a similar fashion as the use of XIC information in mass spectrometry.

TABLE VI

Number of SRA reads associated with top 10 species taxa, for a subset of 14428 reads from a WGS sequencing of a pure *Escherichia coli* sample.

| Species name | Taxid | # Reads | # specific Reads |
|---|---|---|---|
| *Escherichia coli* | 562 | 14421 | 473 |
| *Shigella sonnei* | 624 | 11604 | 0 |
| *Shigella boydii* | 621 | 11276 | 0 |
| *Shigella flexneri* | 623 | 11260 | 0 |
| *Shigella dysenteriae* | 622 | 10422 | 0 |
| *Escherichia fergusonii* | 564 | 6561 | 0 |
| *Salmonella enterica* | 28901 | 2369 | 0 |

TABLE VI-continued

Number of SRA reads associated with top 10 species taxa, for a subset of 14428 reads from a WGS sequencing of a pure *Escherichia coli* sample.

| Species name | Taxid | # Reads | # specific Reads |
|---|---|---|---|
| *Enterobacter cloacae* | 550 | 2180 | 0 |
| *Citrobacter koseri* | 545 | 1973 | 0 |
| *Citrobacter rodentium* | 67825 | 1774 | 0 |

The recent development of RNA-seq allows performing such identification and quantification of organisms present in mixtures taking RNA as starting material for next-generation sequencing of the nucleotide sequences.

2.9 Sample with a Mixture of 2 Closely-Related Organisms: *Escherichia coli* and *Yersinia pestis*, Both from the Enterobacteriaceae Family The proteins from the mixture of the two organisms were extracted, proteolyzed with trypsin, and the resulting peptides analyzed by tandem mass spectrometry.

The NCBI nr database used for data assignation in all this document is dated Feb. 7, 2014 and contains 35,149,712 different protein sequences. The corresponding NCBI taxonomy files are dated Feb. 7, 2014 and correspond to a total of 1,176,883 taxa at all levels. Among these, 12,235 taxa have more than 500 associated protein sequences.

When ordering the taxa by the number of PSMs (decreasing order) as shown in FIG. 10, the mixed nature of the sample (two different organisms) cannot be inferred. The same dataset is presented in FIG. 11 with the additional information of phylogenetic distances between taxa. The fact that this sample is a mixture including two closely-related organisms, *Escherichia coli* and *Yersinia pestis*, is apparent in this display. FIG. 12 shows the decomposition of the signal and the resulting fitting parameters with the method according to the present invention. In all this document, the objective function used is the coefficient of determination noted $R^2$ (or $R^2$) in the fit, and the fit algorithm used is the Levenberg-Marquardt algorithm as implemented in the Python scipy.optimize.leastsq package. In the following signature function:

$$x<d: y=N*(A*\exp(-d/a)+(1-A)*\exp(-d/b))$$

$$x>=d: y=N*(A*\exp(-x/a)+(1-A)*\exp(-x/b)),$$

the fitted parameters where d and N for each signature in the fit, and the fit stopping condition was: $(R^2i+1-R^2i)/R^2i<0.0005$.

2.10. Sample with a Mixture of 3 Different Organisms: *Sphingomonas wittichii* (Alpha-proteobacteria class, Sphingomonadales Order), *Escherichia coli* (Gamma-Proteobacteria Class), and *Ruegeria pomeroyi* (Alpha-Proteobacteria Class, Rhodobacterales Order)

The proteins from the mixture of the three organisms were extracted, proteolyzed with trypsin, and the resulting peptides analyzed by tandem mass spectrometry. When ordering the taxa by the number of PSMs (decreasing order) as shown in FIG. 13 and FIG. 14, the mixed nature of the sample (three different organisms) cannot be inferred. FIG. 13 and FIG. 14 are the display at the species taxonomical level and the most resolved taxonomical level (i.e. strains), respectively. The same dataset is presented in FIG. 15 with the additional information of phylogenetic distance between taxa. The fact that this sample is a mixture including three organisms, *Sphingomonas wittichii*, *Ruegeria pomeroyi*, and *Escherichia coli*, is apparent in this display. FIGS. 16, 17, 18 and 19 show the decomposition of the signal with the method according to the invention, for the same dataset, as well as the resulting fitting parameters, at different taxonomical levels. FIG. 16 shows the first iteration step consisting in obtaining the fit using only the signature signal for *S. wittichii* RW1 (the taxon for which the PSM signal is maximum). The next organism identified in the mixture is the data point with the maximum residual signal, namely *Escherichia coli* BL21(DE3) as evidenced after subtracting the fit to the data points as displayed in FIG. 16, right panel. FIG. 17 shows the final decomposition of the three signals arising from the three organisms analyzed at the most resolved taxonomical level, as well as the resulting fitting parameters. FIG. 18 and FIG. 19 show the final decomposition of the three signals arising from the three organisms analyzed at the species and genus taxonomical levels, respectively, as well as the resulting fitting parameters.

BIBLIOGRAPHY

Ciccarelli, F. D., Doerks, T., von Mering, C., Creevey, C. J., Snel, B. and Bork, P. (2006) Toward automatic reconstruction of a highly resolved tree of life. *Science*, 311 (5765):1283-1287.

Dworzanski, J. P., Deshpande, S. V., Chen, R., Jabbour, R. E., Snyder, A. P., Wick, C. H. and Li, L. (2006) Mass spectrometry-based proteomics combined with bioinformatic tools for bacterial classification. *Journal of Proteome Research*, 5(1):76-87.

Dworzanski, J. P., Dickinson, D. N., Deshpande, S. V., Snyder, A. P. and Eckenrode, B. A. (2010) Discrimination and Phylogenomic Classification of Bacillus anthracis-cereus-thuringiensis Strains Based on LC-MS/MS Analysis of Whole Cell Protein Digests. *Analytical Chemistry*, 82(1):145-155.

Dworzanski, J. P., Snyder, A. P., Chen, R., Zhang, H. Y., Wishart, D. and Li, L. (2004) Identification of bacteria using tandem mass spectrometry combined with a proteome database and statistical scoring. *Analytical Chemistry*, 76(8):2355-2366.

Jabbour, R. E., Deshpande, S. V., Wade, M. M., Stanford, M. F., Wick, C. H., Zulich, A. W., Skowronski, E. W. and Snyder, A. P. (2010) Double-Blind Characterization of Non-Genome-Sequenced Bacteria by Mass Spectrometry-Based Proteomics. *Applied and Environmental Microbiology*, 76(11):3637-3644.

Shokralla, S., Spall, J. L., Gibson, J. F. and Hajibabaei, M. (2012) Next-generation sequencing technologies for environmental DNA research. *Molecular Ecology*, 21(8): 1794-1805.

The invention claimed is:

1. A method of identifying an organism in a sample, the method comprising:
   a) generating a data set concerning one component of the sample, said component being selected from the group consisting of peptide sequences and nucleic acid sequences;
   b) comparing, automatically by a computing device, the data set with a database of known data concerning the component and matching each member of the data set to one or more taxons;
   c) defining by a computing device
      (i) X values along an X axis as a phylogenetic distance,
      (ii) Y values along a Y axis as a number of matches per taxon,
      (iii) taxon k as the taxon with the highest number of matches in the data set, and (iv) signature function as a function modeling a contribution of taxon k to the number of matches per taxon observed for any taxon at a phylogenetic distance between the taxon and taxon k;

d) calculating or assigning, by the computing device, the phylogenetic distance between each taxon and the taxon k;

e) generating, by the computing device, a signature function for taxon k represented by a correlation curve;

f) defining, by the computing device, an objective function selected from the group consisting of sum of squared errors, maximum of errors, and sum of absolute errors; said errors being calculated by subtracting Y values of the signature function relating to taxon k from the Y values assigned at step c) to each taxon; and g) minimizing, by the computing device, the objective function by fitting parameters of the signature function for taxon k, and comparing the objective function with a threshold to determine whether the sample comprises the organism represented by taxon k, the sample comprises an unknown organism, or the sample comprises at least one other detectable organism, wherein:

(i) if the objective function is below the threshold and the signature function represented by the correlation curve intersects the Y axis with a negative slope, the sample comprises the organism represented by taxon k;

(ii) if the objective function is below the threshold and the signature function represented by the correlation curve intersects the Y axis with a zero slope, the sample comprises the unknown organism which is distant from taxon k by the abscissa of the point of the signature function where the slope becomes negative; and (iii) if the objective function is above the threshold, the sample comprises the at least one other detectable organism.

2. The method of claim 1, wherein the component is a peptide sequence, the matches are peptide spectrum matches and the generation of the data set in step a) is performed by tandem mass spectrometry.

3. The method of claim 1 or 2, wherein the signature function in step c) is a monotonic decreasing function.

4. The method of claim 1, wherein the signature function in step c) has the formula:

$$0 < X_k < d_k : Y_k = N_k \times (A_k \times \exp(-d_k/d1_k)) + (1-A_k) \times \exp(-d_k/d2_k))$$

$$d_k < X_k : Y_k = N_k \times (A_k \times \exp(-X_k d1_k) + (1-A_k) \times \exp(-X_k d2_k) \quad \text{Formulae 1}$$

wherein k is the taxon with the highest number of matches in the data set, $N_k$ is the number of matches attributed to taxon k, variable $X_k$ is the phylogenetic distance between each taxon from step b) and taxon k, $Y_k$ is the modelled number of matches due to taxon k attributed to the taxon at distance $X_k$ from taxon k, exp( ) is the exponential function, $A_k$ is the percentage of the exponential term in the form $\exp(-X_k/dl_k)$, with the complement to 1 attributed to the second exponential term in the form $\exp(-X_k/d2_k)$; terms $dl_k$ and $d2_k$ are homogenous to distances representing components shared between taxa due to sequence conservation; $d_k$ represents the phylogenetic distance between the taxon in the sample and taxon k which is the closest taxon in the database.

5. The method of claim 4, wherein in step g), the objective function is minimized by fitting parameters, for each identified taxon k, selected from the group consisting of: $N_k$, $d_k$, $A_k$, $dl_k$ and $d2_k$.

6. A method of identifying several organisms in a sample, comprising performing the method of claim 1 and then repeating steps $d_p$) to $g_p$), $d_p$) calculating or assigning a phylogenetic distance between each of said taxon(s) and a taxon $k_p$ with the highest positive error or the taxon with a number of specific matches;

$e_p$) generating a signature function for said taxon $k_p$, said function being defined as a function modelling a contribution of said taxon $k_p$ to a number of matches per taxon observed for any taxon at said phylogenetic distance between said taxon and taxon $k_p$, said number of matches per taxon defining Y values along a Y axis and said phylogenetic distance defining X values along a X axis;

$f_p$) defining an objective function selected from the group consisting of sum of squared errors, maximum of errors and sum of absolute errors, said errors being calculated by subtracting a sum of the signature functions relating to the taxa k to $k_p$ from the Y values assigned at step b) to each taxon; and $g_p$) minimizing the objective function by fitting parameters of the signature function for taxa k to $k_p$, and comparing the objective function value with a first threshold and/or comparing the objective function change upon repetition with a second threshold, until the objective function value is below a first threshold or the objective function changed upon repetition is below a second threshold.

7. The method of claim 1, wherein taxa are clades at a given taxonomical level.

8. A method of quantifying an organism in a sample, comprising:

aa) identifying an organism in a sample by the method of claim 1, wherein an organism present in the sample is assigned to a taxon, so that there is a match between an organism and a taxon;

bb) substituting the match within said taxon by quantifying the component associated with the match in the sample;

cc) ordering the quantified matches from step bb) by quantity, from highest to lowest and selecting a subset; and dd) quantifying a taxon by a calculation based on the selected subset, using the sum, mean, or median of the subset.

9. A method of quantifying several organisms in a sample comprising:

aa) identifying organisms in a sample according to the method of claim 6, wherein each group of organisms present in the sample is assigned to a taxon, so that there is a match between a group of organisms and a taxon;

bb) substituting each match within said taxon by quantifying the component associated with the match in the sample;

cc) ordering the quantified matches from step bb) by quantity, from highest to lowest and selecting a subset; and dd) quantifying a taxon by a calculation based on the selected subset, using the sum, mean, or median of the subset.

10. The method of claim 8 or claim 9 wherein in step bb) the component is peptide sequences, and the quantifying is performed by a method selected from the group consisting of a method using extracted Ion Chromatograms, a quantification method based on mass spectrometry data or liquid-chromatography data, a tandem mass spectrometry (MS/MS) total ion current and methods based on peptide fragments isolation and quantification selected from the group consisting of selected reaction monitoring (SRM), parallel reaction monitoring (PRM) and multiple reaction monitoring (MRivt).

11. The method of claim 1, wherein step b) is performed iteratively on an increasingly smaller number of taxa, wherein only the taxa identified after repetition of steps c) to g) are retained and then from within these retained taxon(s) further steps b) to g) are repeated at least one time.

* * * * *